(12) United States Patent
Xing

(10) Patent No.: US 9,273,318 B2
(45) Date of Patent: *Mar. 1, 2016

(54) INDUCTION OF THYROID IODIDE-HANDLING GENE EXPRESSION IN HUMAN CANCERS

(71) Applicant: THE JOHNS HOPKINS UNIVERSITY, Baltimore, MD (US)

(72) Inventor: Michael Mingzhao Xing, Clarksville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/147,689

(22) Filed: Jan. 6, 2014

(65) Prior Publication Data

US 2014/0301943 A1 Oct. 9, 2014

Related U.S. Application Data

(62) Division of application No. 12/865,620, filed as application No. PCT/US2009/033214 on Feb. 5, 2009, now Pat. No. 8,653,045.

(60) Provisional application No. 61/063,605, filed on Feb. 5, 2008, provisional application No. 61/119,500, filed on Dec. 3, 2008.

(51) Int. Cl.
*A61K 48/00* (2006.01)
*C07H 21/02* (2006.01)
*C07H 21/04* (2006.01)
*C12N 15/113* (2010.01)

(52) U.S. Cl.
CPC ........ *C12N 15/1137* (2013.01); *C12N 15/1135* (2013.01); *A01K 2217/058* (2013.01); *C12N 2310/14* (2013.01); *C12N 2310/531* (2013.01); *C12N 2320/31* (2013.01)

(58) Field of Classification Search
CPC .............................. A61K 48/00; C12N 15/113
See application file for complete search history.

(56) References Cited

U.S. PATENT DOCUMENTS 6,803,199 B2 * 10/2004 Carrasco et al. ............. 435/6.16
7,560,457 B2 * 7/2009 Graziani et al. ........... 514/229.5

* cited by examiner

*Primary Examiner* — Amy Bowman
(74) *Attorney, Agent, or Firm* — Johns Hopkins Technology Transfer; Guido J. Galvez

(57) ABSTRACT

Dual suppression of the MAP kinase and PI3K/Akt pathways showed synergistic or greatly enhanced anti-melanoma cell effects, compared to suppression of a single pathway, including the inhibition of cell proliferation, transformation and invasion, induction of $G_0/G_1$ cell cycle arrest and, importantly, cell apoptosis. Remarkably, suppression of either pathway induces the expression of thyroid iodide-handling genes and dual suppression of the two pathways synergistically and robustly induces expression of these genes, accompanied by uptake of radioiodine in the cells. These genes include sodium/iodide symporter, thyroid-stimulating hormone receptor, thyroglobulin, thyroperoxidase, pendrin gene, thyroid transcription factors (e.g., TTF-1, TTF-2, PAX8) and other thyroid genes. Targeting major signaling pathways, such as the MAP kinase and PI3K/Akt pathways, for potent cell death, optionally coupled with induction of thyroid gene expression for adjunct radioiodine ablation therapy may be used for many human cancers, both thyroid and non-thyroid.

26 Claims, 17 Drawing Sheets

A

B

INDUCTION OF THYROID IODIDE-HANDLING GENE EXPRESSION IN HUMAN CANCERS

This invention was made using funds from the U.S. government, particularly from the National Institutes of Health. The U.S. government retains certain rights in the invention according to the terms of RO1 CA113507-01.

TECHNICAL FIELD OF THE INVENTION

This invention is related to the area of cancer. In particular, it relates to cancer treatment.

BACKGROUND OF THE INVENTION

Cancer is a major cause of human death. There is currently no cure for many types of human cancers. Many cancers are very aggressive with a high mortality and some have an increasing incidence in recent years. For example, melanoma is a common skin cancer and recent decades have seen a markedly increase in its incidence worldwide (Jemal A, Devesa S S, Hartge P, Tucker M A. Recent trends in cutaneous melanoma incidence among whites in the United States. J Natl Cancer Inst 2001; 93:678-83; Lasithiotakis K G, Leiter U, Gorkievicz R, et al. The incidence and mortality of cutaneous melanoma in Southern Germany: trends by anatomic site and pathologic characteristics, 1976 to 2003. Cancer 2006; 107:1331-9; Ries L A G, Melbert D, Krapcho M, et al. (eds). SEER Cancer Statistics Review, 1975-2005, National Cancer Institute. Bethesda, Md., http://seer.cancer.gov/csr/1975_2005/, based on November 2007 SEER data submission, posted to the SEER web site, 2008). In the United States alone, 62,480 new cases and 8,420 deaths from melanoma were estimated for the year of 2008 (Ries, supra). Although early-stage disease is curable through surgical excision, advanced metastatic melanoma is resistant to current treatments, with a rapidly progressive course and high mortality rate (Flaherty K T. Chemotherapy and targeted therapy combinations in advanced melanoma. Clin Cancer Res 2006; 12:2366s-70s; Tawbi H A, Kirkwood J M. Management of metastatic melanoma. Semin Oncol 2007; 34:532-45).

A major effort in melanoma research has thus been to identify novel treatment strategies targeting major molecular pathways, particularly the Ras→Raf→MEK→MAP kinase/ERK (MAPK) and PI3K/Akt signaling pathways, which are commonly over-activated by genetic alterations, such as the BRAF mutations in the MAPK pathway (Davies H, Bignell G R, Cox C, et al. Mutations of the BRAF gene in human cancer. Nature 2002; 417:949-54) and the PIK3CA amplification and PTEN mutations in the PI3K/Akt pathway (Wu H, Goel V, Haluska F G. PTEN signaling pathways in melanoma. Oncogene 2003 22:3113-22; Curtin J A, Fridlyand J, Kageshita T, et al. Distinct sets of genetic alterations in melanoma. N Engl J Med 2005; 353:2135-47; Marquette A, Bagot M, Bensussan A, Dumaz N. Recent discoveries in the genetics of melanoma and their therapeutic implications. Arch Immunol Ther Exp (Warsz) 2007; 55:363-72). These two pathways play a fundamental role in the pathogenesis and progression of melanoma and are therefore important therapeutic targets for this cancer (Satyamoorthy K, Li G, Gerrero M R, et al. Constitutive mitogen-activated protein kinase activation in melanoma is mediated by both BRAF mutations and autocrine growth factor stimulation. Cancer Res 2003; 63:756-9; Stahl J M, Sharma A, Cheung M, et al. Deregulated Akt3 activity promotes development of malignant melanoma. Cancer Res 2004; 64:7002-10; Dai D L, Martinka M, Li G. Prognostic significance of activated Akt expression in melanoma: a clinicopathologic study of 292 cases. J Clin Oncol 2005; 23:1473-82; Meier F, Schittek B, Busch S, et al. The RAS/RAF/MEK/ERK and PI3K/AKT signaling pathways present molecular targets for the effective treatment of advanced melanoma. Front Biosci 2005; 10:2986-3001; Meier F, Busch S, Lasithiotakis K, et al. Combined targeting of MAPK and AKT signalling pathways is a promising strategy for melanoma treatment. Br J Dermatol 2007; 156:1204-13; Kwong L, Chin L, Wagner S N. Growth factors and oncogenes as targets in melanoma: lost in translation? Adv Dermatol 2007; 23:99-129).

Radioiodine therapy based on the sodium/iodide symporter (NIS) gene transfer has been widely investigated as a potential therapeutic strategy for extrathyroidal malignancies (Faivre J, Clerc J, Gérolami R, et al. Long-term radioiodine retention and regression of liver cancer after sodium iodide symporter gene transfer in Wistar rats. Cancer Res 2004; 64:8045-51; Dwyer R M, Bergert E R, O'Connor M K, et al. In vivo radioiodide imaging and treatment of breast cancer xenografts after MUC1-driven expression of the sodium iodide symporter. Clin Cancer Res 2005; 11:1483-9; Riesco-Eizaguirre G, Santisteban P. A perspective view of sodium iodide symporter research and its clinical implications. Eur J Endocrinol 2006; 155:495-512; Schipper M L, Riese C G, Seitz S, et al. Efficacy of 99mTc pertechnetate and 131I radioisotope therapy in sodium/iodide symporter (NIS)-expressing neuroendocrine tumors in vivo. Eur J Nucl Med Mol Imaging 2007; 34:638-50; Willhauck M J, Sharif Samani B R, Klutz K, et al. Alpha-fetoprotein promoter-targeted sodium iodide symporter gene therapy of hepatocellular carcinoma. Gene Ther 2008; 15:214-23). NIS is normally expressed in the basal membrane of follicular thyroid cells, which transports iodide from blood stream into the cell for the biosynthesis of thyroid hormone (Riesco-Eizaguirre, supra; Nilsson M. Iodide handling by the thyroid epithelial cell. Exp Clin Endocrinol Diabetes 2001; 109:13-17). This process also involves several other key molecules, including thyroglobulin (Tg), which incorporates iodide through organification that involves thyroperoxidase (TPO). Thyroid transcription factor 1 (TTF1 or TITF1) and 2 (TTF2 or FOXE1) and PAX8 are involved in the regulation of these genes. Expression of many of these iodide-handling genes in the thyroid cell is up-regulated by the thyroid-stimulating hormone (TSH), which acts on the TSH receptor (TSHR) in the thyroid cell membrane. This is the molecular basis for the commonly used radioiodide ablation therapy for thyroid cancer, which is clinically facilitated by increasing the level of TSH in the blood of the patient either through thyroid hormone withdrawal or administration of recombinant human TSH (Mian C, Lacroix L, Bidart J.-M, Caillou B, Filetti S, Schlumberger M. Sodium/iodide symporter in thyroid cancer. Exp Clin Endocrinol Diabetes 2001; 109: 47-51; Duntas L H, Cooper D S. Review on the occasion of a decade of recombinant human TSH: prospects and novel uses. Thyroid 2008; 18(5):509-16). In papillary thyroid cancer (PTC), BRAF mutation (and hence activation of the MAPK pathway) was associated with decreased radioiodine avidity (Xing M, Westra W H, Tufano R P, et al. BRAF mutation predicts a poorer clinical prognosis for papillary thyroid cancer. J Clin Endocrinol Metab 2005; 90:6373-9; Riesco-Eizaguirre G, Gutierrez-Martinez P, Garcia-Cabezas M A, Nistal M, Santisteban P. The oncogene BRAF V600E is associated with a high risk of recurrence and less differentiated papillary thyroid carcinoma due to the impairment of Na+/I− targeting to the membrane. Endocr Relat Cancer 2006; 13:257-69; Mian C, Barollo S, Pennelli G, et al. Molecular characteristics in papillary thyroid cancers (PTCs)

with no (131)I uptake. Clin Endocrinol 2008; 68:108-16), which can be explained by BRAF mutation-associated silencing of thyroid iodide-handling genes, such as NIS (Riesco-Eizaguirre G, Santisteban P, supra; Durante C, Puxeddu E, Ferretti E, et al. BRAF mutations in papillary thyroid carcinomas inhibit genes involved in iodine metabolism. J Clin Endocrinol Metab 2007; 92:2840-3), Tg (Durante, supra), and TPO (Mian, supra; Durante, supra; Giordano T J, Kuick R, Thomas D G, et al. Molecular classification of papillary thyroid carcinoma: distinct BRAF, RAS, and RET/PTC mutation-specific gene expression profiles discovered by DNA microarray analysis. Oncogene 2005; 24:6646-56; Di Cristofaro J, Silvy M, Lanteaume A, Marcy M, Carayon P, De Micco C. Expression of tpo mRNA in thyroid tumors: quantitative PCR analysis and correlation with alterations of ret, Braf, ras and pax8 genes. Endocr Relat Cancer 2006; 13:485-95). Several previous studies also demonstrated involvement of the PI3K/Akt pathway in the regulation of thyroid iodide-handling genes. For example, expression of a mutant Ras that selectively stimulated the PI3K/Akt pathway markedly decreased TSH-induced NIS expression (Cass L A, Meinkoth J L. Ras signaling through PI3K confers hormone-independent proliferation that is compatible with differentiation. Oncogene. 2000; 19:924-32) and IGF-I could inhibit cAMP-induced NIS expression through activating the PI3K/Akt pathway (Garcia B, Santisteban P. PI3K is involved in the IGF-I inhibition of TSH-induced sodium/iodide symporter gene expression. Mol Endocrinol 2002; 16:342-52) in thyroid cells.

In recent clinical trials on various human cancers, including melanoma, targeting an individual pathway, such as the MAPK pathway or the PI3K/Akt pathway, or use of a single agent generally failed to show significant clinical responses (Marquette, supra; Kwong, supra; Friday B B and Adjei A A. Advances in targeting the Ras/Raf/MEK/Erk mitogen-activated protein kinase cascade with MEK inhibitors for cancer therapy. Clin Cancer Res 2008; 14:342-6). A recent study showed common expression of TSHR in melanoma cells, but no or little expression in benign skin lesions (Ellerhorst J A, Sendi-Naderi A, Johnson M K, Cooke C P, Dang S M, Diwan A H. Human melanoma cells express functional receptors for thyroid-stimulating hormone. Endocr Relat Cancer 2006; 13:1269-77), raising the possibility that other thyroid iodide-handling genes might also be expressible in melanoma cells.

There is a continuing need in the art to develop more effective treatments for human cancers.

SUMMARY OF THE INVENTION

According to one aspect of the invention a method is provided for treating a human cancer in a patient. An inhibitor of a PI3K/Akt pathway protein or its expression is administered to the patient. And an inhibitor of a MAP kinase pathway protein or its expression is administered to the patient. The inhibitors are administered in sufficient amounts to induce expression of one or more iodide-handling genes in the human cancer.

According to another aspect of the invention a method is provided for treating a human cancer in a patient. An inhibitor of a PI3K/Akt pathway protein or its expression or of a MAP kinase pathway protein or its expression is administered to the patient in sufficient amounts to induce expression of one or more iodide-handling genes in the human cancer. And radioiodine is administered to the patient.

Yet another aspect of the invention provides a method for treating a melanoma or a thyroid cancer in a human. An inhibitor of a PI3K/Akt pathway protein or its expression and an inhibitor of a MAP kinase pathway protein or its expression are administered to the patient in sufficient amounts to induce expression of one or more iodide-handling genes in the melanoma or thyroid cancer. And radioiodine is administered to the human.

A further aspect of the invention is a kit. The kit comprises in a divided or undivided container at least two of the following therapeutic agents: an inhibitor of a PI3K/Akt pathway protein or its expression, an inhibitor of a MAP kinase pathway protein or its expression, and radioiodine.

These and other embodiments which will be apparent to those of skill in the art upon reading the specification provide the art with new ways to effectively treat human cancers.

BRIEF DESCRIPTION OF THE DRAWINGS

FIG. 1A) Inhibition of ERK and Akt phosphorylation by suppression of MAPK and PI3K/Akt pathways using the MEK-specific inhibitor U0126 and the Akt-specific inhibitor Akti IV, respectively. NPA cells were treated with U0126 at 10 μM, or with Akti IV at 0.5 μM for 30 h. Cells were lysed for Western blotting assay. The activities of MAPK and PI3K/Akt pathways were reflected by the level of phosphorylated ERK and Akt detected with specific anti-phosphorylated ERK (p-ERK) and anti-phosphorylated Akt (p-Akt) antibodies. Immunoblotting with antibody against β-actin was used for quality control. FIG. 1B) Inhibition of cell proliferation by suppression of MAPK and PI3K/Akt pathways achieved with U0126 and Akti IV individually or in combination (U+A) as indicated. MTT assay was performed to evaluate cell proliferation over a 5-day course of treatment with U0126 and Akti IV. NPA cells were treated with 4 μM U0126 and 0.2 μM Akti IV, respectively—lower concentrations than those in FIG. 1A) were used for the two inhibitors in order to examine their additive/synergist effects. FIG. 1C) Expression of thyroid genes by dual suppression of MAPK and PI3K/Akt pathways using U0126 and Akti IV. For expression analysis of thyroid genes (NIS, TSHR, Tg, TPO, FOXE1, and TTF1), total RNA was isolated and RT-PCR was performed 30 h after cells were treated with U0126 and Akti IV individually or combination at the concentrations used in FIG. 1A).

FIG. 3A) NPA cells were infected with lentivirus expressing BRAF or Akt-1/2 siRNAs or both and stable populations were selected with 2 μg/ml puromycin. The empty vector was used as the control. After a 2-week selection, cells were lysed and immunoblotted with BRAF, Akt-1 and Akt-2 antibodies. The antibody against β-actin was used for quality control of Western blotting. FIG. 3B) Proliferation rate of NPA cells stably transfected with various siRNA constructs as described in FIG. 3A) was measured with MTT assay daily over a 5-day course. Results are expressed as means±SD of three independent experiments.

FIG. 3C) Representative results of colony formation in soft agar of thyroid cancer cells with stable transfections with different siRNA constructs, including empty vector (vector), BRAF siRNA (BRAF KD), Akt-1/2 siRNA (Akt-1/2 KD), and combination of Akt-1/2 and BRAF siRNA (BRAF+Akt-1/2 KD). Data represent means±SD of three independent experiments. KD, knockdown (same as in all other Figures).

FIG. 4A) Shown are representative results of invasive NPA cells. FIG. 4B) The bar graphs, corresponding to (FIG. 4A), show means±SD of the numbers of invading cells from three independent experiments.

FIG. 6A) NPA cells were stably transfected with specific siRNAs to knock down BRAF and Akt-1/2, individually or dually as described in FIG. 3. After a serum starvation for 24 h, total RNA was isolated for expression analysis for the indicated thyroid iodide-metabolizing genes. RT-PCR analysis was performed for the expression of NIS in NPA cells. FIG. 6B) Flow cytometric measurement of NIS protein expression. NPA cells were treated with specific inhibitors (upper panel) as described in FIG. 1 or stably transfected with specific siRNAs to knock down BRAF and Akt-1/2, individually or in combination as described in FIG. 3 (lower panel). NIS protein levels were measured by flow cytometry. The blue frames indicate the cells expressing NIS protein, including dead (right upper quadrant; positive for both 7-AAD and NIS) and living (right lower quadrant, positive only for NIS) cells. FIG. 6C) Immunofluorescent localization of NIS. After a 30-h combined treatment with both U0126 and Akti IV (as in FIG. 6B), cells were analyzed by immunofluorescent microscopy using anti-NIS and FITC-coupled secondary antibody and double immunofluorescence with the red color representing 7-AAD nuclear staining and the green color representing NIS expression and localization. Cells marked with dash circles are intact living cells that do not have 7-AAD nuclear staining NIS staining in these cells represents NIS protein expression exclusively on the cell membrane. Cells marked with solid circles show double colors, suggesting that the cells were not intact and therefore both cell membrane NIS staining and 7-AAD nuclear staining occurred. The NIS expression is in striking contrast with the control cells which did not show any NIS staining even in the broken cells that showed nuclear staining (red color) with 7-ADD. FIG. 6D) In vitro radioiodide uptake. NPA cells were treated with specific inhibitors or stably transfected with various siRNA constructs as indicated. Cells were subsequently incubated with 1 µCi $^{125}$I/0.5 ml/well on 12-well plates for 1 h. Cells were then washed and harvested for radioactivity measurement using a gamma-counter as described in the Materials and Methods. Data are expressed as the mean±SD of values from three assays. **, P<0.01, compared with control or empty vector.

FIG. 7A-7C. Effects of suppression of the PI3K/Akt and MAP kinase pathways by specific inhibitors on thyroid cancer cells. FIG. 7B) Inhibition of thyroid cancer cell proliferation by suppression of PI3K/Akt and MAP kinase pathways achieved with Akti IV and U0126 individually or in combination (U+A) as indicated. MTT assay was performed to evaluate cell proliferation over a 5-day course of treatment with Akti IV and U0126. One µM Akti IV for KAT10 cells and 0.2 µM Akti IV for NPA cells and 4 µM U0126 for both cells were used lower concentrations than those in FIG. 7A) were used for the two inhibitors in order to examine their additive/synergist effects. FIG. 7C) Synergistic re-expression of thyroid genes by dual suppression of PI3K/Akt and MAP kinase pathways using Akti IV and U0126. For expression analysis of thyroid genes (Tg, TSHR, NIS, TTF-1, and TTF2), total RNA was isolated and quantitative real-time PCR was performed 30 h after cells were treated with Akti IV and U0126 individually or combination at the concentrations used in FIG. 7A). The value for each gene represents the mean of triplicate measurements.

FIG. 8A) KAT10 cell clones stably transfected with BRAF-specific siRNA (clone C9) and control scrambled siRNA (clone 2B2) were superinfected with shRNA vectors targeting Akt-1 or Akt-2. Empty vectors (V) were used as controls. Two different sets of siRNA sequences (A and B) for Akt-1 and Akt-2 were used as described in the Experimental Procedures. Cells were lysed and immunoblotted with Akt isoform- or BRAF-specific antibodies as indicated. Immunoblotting with antibody against β-actin was used for quality control of Western blotting. Set A of siRNA sequences were used in the experiments in FIGS. 8B, 8C, and 8D. FIG. 8B) Fluorescent microscopy of 2B2 and C9 cell clones superinfected with GFP-containing constructs to knock down Akt-1 or Akt-2 (indicated as Akt-1 KD and Akt-2 KD, respectively). Empty vectors were used as control. At two weeks of cell culture, GFP expression was examined using a fluorescent microscope (Nikon Eclipse TE300, NY) to confirm the high efficiency and stability of transfection. FIG. 8C) Effect of Akt-1 or Akt-2 and BRAF knockdown on cell proliferation. 2B2 and C9 cell clones superinfected with empty vector, Akt-1 or Akt-2 shRNA were grown in triplicates of culture for the indicated days, with initial seeding of 800 cells per well. MTT assay was performed daily to evaluate cell proliferation (means±SD of triplicate). FIG. 8D) Colony formation assays were performed to evaluate anchorage-independent growth of 2B2 and C9 cell clones after superinfection with Akt-1 or Akt-2 siRNA. After culture in soft agar for 3 wk, colonies were counted and photographed. A representative experiment of colony formation with various shRNA constructs is presented with a corresponding bar graph (right panel) showing the mean±SD of colony numbers from three independent experiments. KD, knockdown (same as in all other Figures).

FIG. 9A) NPA and KAT10 cells were infected with lentivirus expressing Akt-1/2 or BRAF siRNAs or both and stable populations were selected with 2 µg/ml puromycin. Empty vector was used as control. After a 2-week selection, cells were lysed and immunoblotted with Akt-1, Akt-2, and BRAF antibodies. The antibody against β-actin was used for quality control of Western blotting. FIG. 9B) Proliferation rate of thyroid cancer cells stably transfected with various siRNA constructs as described for A) was measured with MTT assay daily over a 5-day course. Results are expressed as means±SD of three independent experiments. FIG. 9C) Representative results of colony formation in soft agar of thyroid cancer cells with stable transfections with different siRNA constructs, including empty vector (a), Akt-1/2 siRNA (b), BRAF siRNA (c), and combination of Akt-1/2 and BRAF siRNA (d). Data represent means±SD of three independent experiments.

FIG. 12A) Time course of tumor growth over 3.5 weeks with stable knockdown of the indicated proteins. Tumor size was measured on the surface of the skin, and tumor volume was calculated as described in the Experimental Procedures. Each time point represents the mean±SD of the values obtained from five mice in each group. FIG. 12B) Shown are the weights of individual tumors surgically removed from mice in each group after their sacrifice. **The P value was obtained by t-test for paired comparison with vector. FIG. 12C) Shown are representative images of tumor-bearing mice at 2 and 3.5 weeks and their tumors after surgical removal from mice.

FIG. 13C) Regular RT-PCR analysis of NIS expression to confirm the results obtained by quantitative real-time PCR.

FIG. 14A) Flow cytometric measurement of NIS protein expression. NPA and KAT10 cells were treated with specific inhibitors (FIG. 14A, upper panel) as described in FIG. 7D or stably transfected with specific siRNAs to knock down Akt-1/2 and BRAF, individually or in combination as described in FIG. 9 (A, lower panel). NIS protein levels were measured by flow cytometry. The blue frames indicate the cells expressing NIS protein, including dead (right upper quadrant; positive for both 7-AAD and NIS) and living (right lower quadrant, positive only for NIS) cells. FIG. 14B) Immunofluorescent localization of NIS. After a 30-h combined treatment with both Akti IV and U0126 (as in FIG. 14A), cells were analyzed by immunofluorescent microscopy using anti-NIS and FITC-coupled secondary antibody and double immunofluorescence with the red color representing 7-AAD nuclear staining and the green color representing NIS expression and localization. Cells marked with dash circles are intact living cells that do not have 7-AAD nuclear staining NIS staining in these cells represents NIS protein expression exclusively on the cell membrane. Cells marked with solid circles show double colors, suggesting that the cells were not intact and therefore NIS staining could be both intracellular and on the cell membrane. In either type of cells, the NIS expression is in striking contrast with the control cells which did not show any NIS staining even in the broken cells that showed nuclear staining (red color) with 7-ADD. FIG. 14C) In vitro radioiodide uptake. NPA and KAT10 cells were treated with specific inhibitors or stably transfected with various siRNA constructs as indicated. Cells were subsequently incubated with 1 µCi Na125I/0.5 ml/well on 12-well plates for 1 h. Cells were then washed and harvested for radioactivity measurement using a gamma-counter as described in the Experimental Procedures. Data are expressed as the mean±SD of values from three assays. **, P<0.01, compared with control or empty vector.

DETAILED DESCRIPTION OF THE INVENTION

Figure 1:
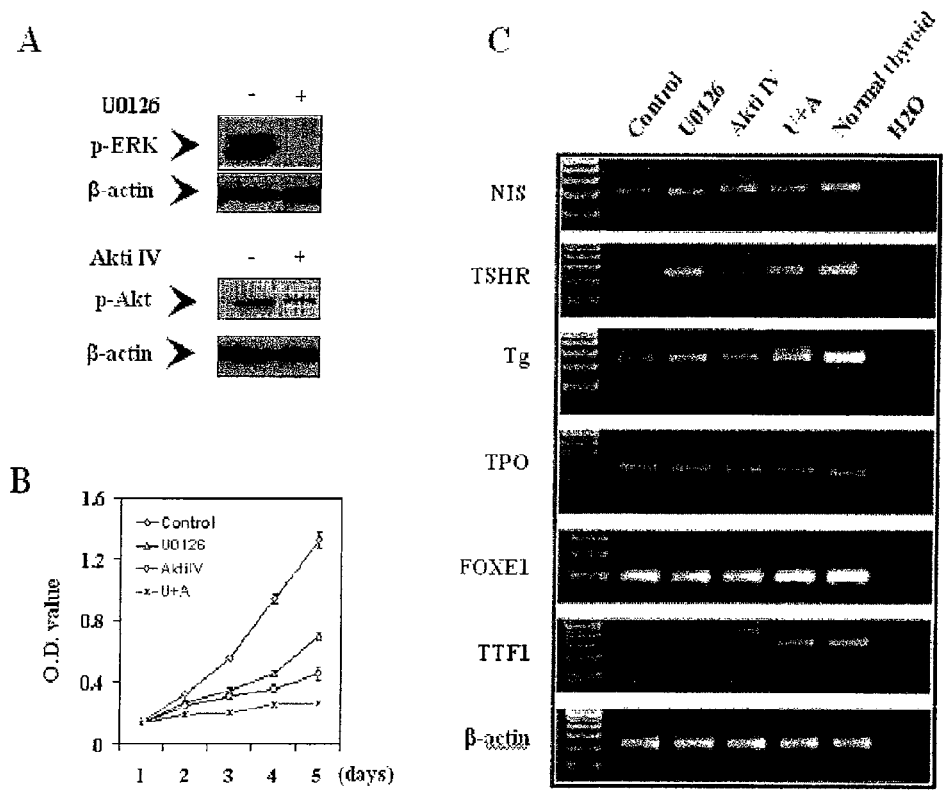
FIGS. 1A-1C Effects of suppression of the MAPK and PI3K/Akt pathways by specific inhibitors on NPA cells.

The inventors have developed methods of treating human cancers which employ inhibitors to suppress MAP kinase and PI3K/Akt pathways. Surprisingly, while suppression of individual pathways provides only a cytostatic effect on cancer cells, suppression of both provides a cytotoxic effect. Remarkably, use of such inhibitors has also been found to induce expression of genes encoding iodide-handling proteins. As a consequence of such induced expression, radioiodine can be administered and its uptake, which is normally seen mainly in thyroid cells, can be used for ablation therapy in cells that previously expressed none or insufficient amounts of such proteins. Such cells include thyroid cancer cells that were previously refractory to radioiodine and non-thyroid cancer cells that were refractory to radioiodine.

Types of human cancers which may be treated as described here include both thyroid and non-thyroid cancers. In particular, the methods are useful in cases of thyroid cancer that have become unable to take up iodide. These are often the least differentiated types of thyroid cancers, i.e., the poorly differentiated and the undifferentiated types, such as anaplastic carcinomas. In addition, even cell types that normally do not have the ability to take up iodide, i.e., non-thyroid cells, can become susceptible to therapy with radioiodide, by virtue of the induction of expression of the genes encoding iodide handling proteins. Suitable cancers for treatment thus include without limitation salivary cancer, lacrimal cancer, stomach cancer, colon cancer, liver cancer, breast cancer, and other cancers. Even in the case where a normal cell type expresses some level of the iodide handling proteins, treatment according to the invention can enhance expression of the proteins. Additional tumor types that may be treated include, without limitation, brain cancers, lymphoma, leukemia, sarcomas, pancreatic cancer, liver, cancer, and myeloma. Other types of cancer which may be treated include cancer of the bladder, rectum, kidney, lung (small cell lung cancer, and non-small-cell lung cancer), esophagus, gall-bladder, ovary, cervix, thyroid, prostate, and skin (including squamous cell carcinoma); tumors of mesenchymal origin (including fibrosarcoma and rhabdomyosarcoma, and other sarcomas, e.g., soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma). Other cancers that can be treated with agents of the present invention include endometrial cancer, head and neck cancer, glioblastoma, malignant ascites, and other hematopoietic cancers.

The cancers that are to be treated may or may not have activating mutations in the MAP kinase or PI3K/Akt pathways. Activating mutations, if present may be in any gene in the pathways, and may be due to point mutation or rearrangement or amplification, as examples.

Agents that can be used to suppress major signaling pathways to inhibit cells and induce thyroid gene expression and radioiodine uptake in human cancers include, but are not limited to, the inhibitors of the MAP kinase pathways, e.g., MEK inhibitors, such as CI-1040, PD0325901, AZD6244, RDEA119, RDEA436; Raf inhibitors, such as PLX4720, BAY 43-9006 (sorafenib); inhibitors of the PI3K/Akt pathway, e.g., Akt inhibitors, such as perifosine and triciribine; mTOR inhibitors, such as temsirolimus, everolimus; receptor tyrosine kinase inhibitors, e.g., motesanib, axitinib, sunitinib; and inhibitors of other signaling pathways, such as the NF-kappa pathway. Individual members of the PI3K/Akt pathway are well known in the art and include: PIK3CA, PIK3D, PIK3B, Ras, and PTEN. Members of the MAP kinase pathway include receptor tyrosine kinases, Grb-2, mSOS, Rsk1, BRAF, RET/PTC, Ras, MEK, and ERK. When two pathways are to be inhibited, two distinct inhibitors of two distinct proteins can be used. Multiple inhibitors of each pathway may also be used, if desired. Certain inhibitors such as Ras inhibitors may act on both pathways and these may also be used in the invention.

Agents for suppression of major signaling pathways can also inhibit expression. Means of inhibition include siRNA, antisense RNA, antisense RNA vectors, miRNA, and other means. Antisense constructs, antisense oligonucleotides, RNA interference constructs, miRNA or siRNA duplex RNA molecules can be used to interfere with expression of a desired pathway member protein. Typically at least 15, 17, 19, or 21 nucleotides of the complement of a desired pathway member protein mRNA sequence are sufficient for an antisense molecule. Typically at least 19, 21, 22, or 23 nucleotides of a desired pathway member protein are sufficient for an RNA interference molecule. Preferably an RNA interference molecule will have a 2 nucleotide 3' overhang. If the RNA interference molecule is expressed in a cell from a construct, for example from a hairpin molecule or from an inverted repeat of the desired pathway member protein sequence, then the endogenous cellular machinery will create the overhangs. siRNA molecules can be prepared by chemical synthesis, in vitro transcription, or digestion of long dsRNA by Rnase III or Dicer. These can be introduced into cells by transfection, electroporation, or other methods known in the art. See Hannon, G J, 2002, RNA Interference, *Nature* 418: 244-251; Bernstein E et al., 2002, The rest is silence. RNA 7: 1509-1521; Hutvagner G et al., RNAi: Nature abhors a double-strand. *Curr. Opin. Genetics & Development* 12: 225-232; Brummelkamp, 2002, A system for stable expression of short interfering RNAs in mammalian cells. *Science* 296: 550-553; Lee N S, Dohjima T, Bauer G, Li H, Li M-J, Ehsani A, Salvaterra P, and Rossi J. (2002). Expression of small interfering RNAs targeted against HIV-1 rev transcripts in human cells. *Nature Biotechnol.* 20:500-505; Miyagishi M, and Taira K. (2002). U6-promoter-driven siRNAs with four uridine 3' overhangs efficiently suppress targeted gene expression in mammalian cells. *Nature Biotechnol.* 20:497-500; Paddison P J, Caudy A A, Bernstein E, Hannon G J, and Conklin D S. (2002). Short hairpin RNAs (shRNAs) induce sequence-specific silencing in mammalian cells. *Genes & Dev.* 16:948-958; Paul C P, Good P D, Winer I, and Engelke D R. (2002). Effective expression of small interfering RNA in human cells. *Nature Biotechnol.* 20:505-508; Sui G, Soohoo C, Affar E-B, Gay F, Shi Y, Forrester W C, and Shi Y. (2002). A DNA vector-based RNAi technology to suppress gene expression in mammalian cells. *Proc. Natl. Acad. Sci. USA* 99(6):5515-5520; Yu J-Y, DeRuiter S L, and Turner D L. (2002). RNA interference by expression of short-interfering RNAs and hairpin RNAs in mammalian cells. *Proc. Natl. Acad. Sci. USA* 99(9):6047-6052.

Antisense or RNA interference molecules can be delivered in vitro to cells or in vivo, e.g., to tumors of a mammal. Typical delivery means known in the art can be used. For example, delivery to a tumor can be accomplished by intratumoral injections. Other modes of delivery can be used without limitation, including: intravenous, intramuscular, intraperitoneal, intraarterial, local delivery during surgery, endoscopic, subcutaneous, and per os. In a mouse model, the antisense or RNA interference can be adminstered to a tumor cell in vitro, and the tumor cell can be subsequently administered to a mouse. Vectors can be selected for desirable properties for any particular application. Vectors can be viral or plasmid. Adenoviral vectors are useful in this regard. Tissue-specific, cell-type specific, or otherwise regulatable promoters can be used to control the transcription of the inhibitory polynucleotide molecules. Non-viral carriers such as liposomes or nanospheres can also be used.

Suppression of other major signaling pathways may also be used in concert with one or more of the inhibitors discussed above. These pathways include without limitation, the NFkappa pathway. Additional mechanisms which may be used in concert include agents to alter epigenetic states, such as histone deacetylase inhibitors and DNA demethylating agents. Another additional means of inducing thyroid iodide-handling gene expression is to administer thyroid-stimulating hormone or an analogue such as human recombinant human TSH, Thyrogen™. Any means of inducing the expression of thyroid genes can be used alone or in concert with others, so that radioiodine treatment can become effective for tumor ablation. Induced expression of may be an increase of at least 25%, at least 50%, at least 75%, at least 100%, at least 2-fold, at least 5-fold, at least 10-fold, at least 20-fold. Maximal induction in any particular tumor or tumor type of iodide-handling gene expression is desirable. Any suitable isotope of iodine can be used, including but not limited to $^{125}$I and $^{131}$I.

Suitable histone deacetylase inhibitors include: hyroxamic acids, such as Trichostatin A, cyclic tetrapeptides (such as trapoxin B), and the depsipeptides, benzamides, electrophilic ketones, Panobinostat and aliphatic acid compounds such as phenylbutyrate and valproic acid. Additional inhibitors include SAHA/Vorinostat, Belinostat/PXD101, M275, LAQ824/LBH589, CI994, MGCD0103, nicotinamide, as well derivatives of NAD, dihydrocoumarin, naphthopyranone, and 2-hydroxynaphaldehydes. Suitable DNA demethylating agents include, without limitation, 5-azacytidine (azacitidine) and 5-azadeoxycytidine (decitabine).

Agents for inhibition can be administered to the patient using any appropriate means known in the art, including oral, intravenous, intramuscular, intrathecal, topical, and subcutaneous administrations. These compositions may be formulated for in vivo administration by dispersion in a pharmacologically acceptable solution or buffer. Suitable pharmacologically acceptable solutions include neutral saline solutions buffered with phosphate, lactate, Tris, and the like.

Since one aspect of the present invention contemplates the treatment of cancers with a combination of pharmaceutically active agents that may be administered separately, the invention further relates to combining separate pharmaceutical compositions in kit form. The kit comprises at least two separate pharmaceutical substances. The kit comprises a container for containing the separate compositions such as a divided bottle or a divided foil packet. Alternately the kit may have at least two of the substances in combination in an undivided container. Additional examples of containers include syringes, boxes and bags. Typically, the kit comprises directions for the use of the components. The kit form is particularly advantageous when the separate components are preferably administered in different dosage forms (e.g., oral and parenteral), are administered at different dosage intervals, or when titration of the individual components of the combination is desired by the prescribing physician or veterinarian.

The compounds of the present invention can be administered as pharmaceutically acceptable salts, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

The inhibitors can be administered as prodrugs. The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

Recent advances in understanding aberrant signaling of molecular pathways in melanoma provide the bases for the current development of novel therapies for this cancer. Of particular importance are the MAPK and PI3K/Akt pathways, which, through their genetic alterations, play a critical role in the development and pathogenesis of melanoma and are therefore tested vigorously as important therapeutic targets for this cancer (6, 10-15). Several clinical trials targeting these pathways in various cancers, including melanoma, have been recently completed (9, 15, 32). Disappointingly, however, little or no anti-tumor response has been achieved in these trials, which were single-agent based and, hence, targeted limited pathways. It becomes increasingly questionable whether targeting only single or limited pathways is an effective therapeutic strategy for cancers (15,32). Given the importance of both the MAPK and PI3K/Akt pathways in melanoma, simultaneously targeting the two pathways, instead of either alone, may prove to be a particularly effective therapeutic strategy for this cancer. In the present study, we tested this hypothesis by dually and specifically suppressing the MAP kinase and PI3K/Akt pathways in melanoma cells and examining molecular and cellular consequences. Our main theme in this effort was to particularly test a novel therapeutic strategy of inducing both potent cellular inhibition and thyroid iodide-handling gene expression for potential adjunct radioiodide therapy for melanoma.

In addition to using specific inhibitors of the pathways, we used shRNA approaches to simultaneously and specifically knock down Akt-1/2 and BRAF, resulting in synergistic/additive inhibition of melanoma cell proliferation, colony formation and invasion, as well as apoptosis. Due to the technical complexities and laborious efforts required in shRNA approaches for simultaneous knockdown of multiple signaling pathways, previous studies on certain cancer cell lines, including one in melanoma cells (14), only attempted using drug inhibitors for simultaneous suppression of the MAPK and PI3K/Akt pathways. The present study represents the first to use the shRNA approach to simultaneously and specifically knock down the MAPK and PI3K/Akt signaling in cancer cells, definitely demonstrating the therapeutic potential of dually targeting the two pathways for cancers, such as melanoma. Of particular note in the present study is that although suppression of either the MAPK or PI3K/Akt pathway could cause significant inhibition of melanoma cell proliferation, suppression of either alone caused little cell apoptosis. Previous studies targeting single pathways using single agents also only showed cell cycle arrest at the $G_0/G_1$ phase, but not apoptosis, in certain cancer cells (39, 40). These results are consistent with the recent clinical trials on melanoma using single agents that showed little anti-tumor effect other than only tumor stability in some cases (9,15,32). Remarkably, the present study showed that combined suppression of the MAPK and PI3K/Akt pathways synergistically promoted cell apoptosis, suggesting that both pathways need to be removed to induce melanoma cell death. This result is consistent with an interesting previous observation that either pathway was sufficient to protect melanoma cells from anoikis, a type of apoptosis induced by loss of normal cell contact (41). Thus, therapeutic approaches dually targeting the MAPK and PI3K/Akt pathways are likely to be more effective in killing melanoma cells harboring genetic alterations that activate both pathways. Consequently, it may be expected that a clinical trial using combined agents targeting both the MAPK and PI3K/Akt pathways would likely show significant anti-melanoma effectiveness, unlike the recently completed single agent-based clinical trials (9,15,32).

Radioiodine ablation therapy is an effective and standard treatment for thyroid cancer, which is routinely administered after thyroidectomy in most thyroid cancer patients (22,23, 42,43). This treatment takes advantage of the unique iodide-handling machinery in thyroid cells, involving several key molecules, such as NIS, TSHR, TPO, Tg, and several thyroid transcription factors. These genes are frequently silenced in thyroid cancer, particularly in association with aberrant activation of the MAPK and PI3K/Akt pathways (18,26-29,44). Suppression of the MAPK and PI3K/Akt pathways could restore the expression of thyroid iodide-handling genes in thyroid cancer cells (39, and Hou and Xing, unpublished data). A previous study interestingly showed that melanoma cells also expressed TSHR (33). Based on these data, we suspected that melanoma cells might have the ability to express other thyroid iodide-handling genes that were regulated by the MAPK and PI3K/Akt pathways. This was interestingly proven to be the case in the present study. In fact, we demonstrated that suppression of either of the two pathways could induce expression of many of these genes and dual suppression of the two pathways had a synergistic/additive effect on their expression in melanoma cells. As an example, NIS, the most important molecule involved in thyroid cellular uptake of iodide, was robustly expressed in the cell membrane with dual suppression of the MAPK and PI3K/Akt pathways either using inhibitors or specific shRNA approaches. As in normal thyroid cells, TSH significantly enhanced the expression of these genes induced by suppression of the MAPK and PI3K/Akt pathways in melanoma cells. Importantly, we also demonstrated that expression of thyroid iodide-handling genes effectively conferred melanoma cells the ability to take up radioiodide. These results have important novel therapeutic implications for melanoma: radioiodide ablation, as in thyroid cancer, might be therapeutically effective for melanoma in conjunction with the use of agents to inhibit the MAPK and PI3K/Akt pathways. For radioiodide treatment of thyroid cancer, TSH is routinely raised either by thyroxine withdrawal or administration of human recombinant TSH to enhance radioiodide uptake and ablation of thyroid cancer cells (21,23,42,43). This strategy could be similarly used for melanoma given the expression of TSHR induced by suppressing the MAKP and PI3K/Akt pathways and the enhancement of expression of other iodide-metabolizing genes by TSH in melanoma cells demonstrated in the present study. In recent years, NIS gene transfer therapy to confer non-thyroid cancers the sensitivity to radioiodide ablation therapy has been widely investigated as a potential therapeutic strategy for human cancers (18,45,46). Yet, the technical complexities, inadequate therapeutic efficiencies, and other issues associated with NIS gene transfer have so far prevented it from rapid and successful clinical use. Our demonstration of the inducibility of thyroid iodide-handling genes and radioiodide uptake in melanoma cells opened the possibility for a potentially safe, effective, and easy alternative approach to therapeutic use of radioiodide in melanoma. Given the results in the present study, it is attractive to propose clinical trials to test the novel therapeutic strategy of simultaneously targeting the MAPK and PI3K/Akt pathways for both synergistic/additive cellular inhibition and thyroid gene expression for adjunct radioiodide treatment in melanoma. Such clinical tries are feasible particularly given the current availability of several safe and potent inhibitors of the MAPK and PI3K/Akt pathways, such as the MEK and Akt inhibitors (9,15,32).

Clinical experience with radioiodine body scan use for thyroid cancer patients often shows uptake of the radiotracer in the stomach, breast, liver, colon, salivary glands, lacrimal glands and other organs, suggesting the natural expression of some of thyroid-iodide genes in these organs. We hypothesize that cancers developed in these organs may also be induced to robustly express thyroid iodide-handling genes by inhibiting the aberrant signaling pathways in these cancers and therefore be conferred the ability to avidly take up radioiodine. We therefore propose that the novel therapeutic strategy demonstrated here for melanoma can be applied also to cancers originated in these organs and many other human cancers.

The majority of deaths from thyroid cancer are caused by PDTC and UTC. These cancers, particularly, UTC, are aggressive and usually do not respond to radioiodine ablation treatment due to the loss of expression of thyroid iodide-metabolizing genes Gilliland F D, Hunt W C, Morris D M, Key C R. Prognostic factors for thyroid carcinoma. A population-based study of 15,698 cases from the Surveillance, Epidemiology and End Results (SEER) program 1973-1991. *Cancer.* 1997; 79:564-573; Cornett W R, Sharma A K, Day T A, et al. Anaplastic thyroid carcinoma: an overview. *Curr Oncol Rep.* 2007; 9:152-158; Sanders E M Jr, LiVolsi V A, Brierley J, Shin J, Randolph G W. An evidence-based review of poorly differentiated thyroid cancer. *World J Surg.* 2007; 31:934-945). There is currently no effective medical treatment for radioiodine non-avid thyroid cancers and death or morbidity of patients usually ensues when the cancer becomes surgically inoperable. There is an urgent need for the development of effective treatments for these patients. The recent progress in understanding the molecular bases, particularly genetic alterations underlying the pathogenesis of aggressive thyroid cancers, provides a unique opportunity to develop novel therapeutic strategies.

In the present study, we proposed that dually targeting the PI3K/Akt and MAP kinase pathways would be therapeutically effective for PDTC and UTC. This hypothesis was based on three molecular bases: 1) Both of the two signaling pathways have been well documented to play a fundamental role in tumorigenesis of many human cancers and are potential therapeutic targets in these cancers (Kohno M, Pouyssegur J. Targeting the ERK signaling pathway in cancer therapy. *Ann Med.* 2006; 38:200-211; Marone R, Cmiljanovic V, Giese B, Wymann M P. Targeting phosphoinositide 3-kinase-Moving towards therapy. *Biochim Biophys Acta.* 2007 Oct. 12; [Epub ahead of print]); 2) Activating genetic alterations in the two pathways are extremely common in thyroid cancers, with an increasing prevalence and overlap from differentiated thyroid tumors to PDTC and UTC (1 Garcia-Rostan G, Costa A M, Pereira-Castro I, et al. Mutation of the PIK3CA gene in anaplastic thyroid cancer. *Cancer Res.* 2005; 65:10199-1020; Kondo T, Ezzat S, Asa S L. Pathogenetic mechanisms in thyroid follicular-cell neoplasia. *Nat Rev Cancer.* 2006; 6:292-306; Hou P, Liu D, Shan Y, et al. Genetic alterations and their relationship in the phosphatidylinositol 3-kinase/Akt pathway in thyroid cancer. *Clin Cancer Res.* 2007; 13:1161-1170; Costa A M, Herrero A, Fresno M F, et al. BRAF mutation associated with other genetic events identifies a subset of aggressive papillary thyroid carcinoma. *Clin Endocrinol.*

2007 Dec. 5; [Epub ahead of print]; Santarpia L, El-Naggar A K, Cote G J, Myers J N, Sherman S I. PI3K/Akt and Ras/Raf-MAPK pathway mutations in anaplastic thyroid cancer. *J Clin Endocrinol Metab.* 2008; 93:278-284); and 3) We in fact have recently demonstrated that genetic alterations that may aberrantly activate receptor tyrosine kinases and the downstream PI3K/Akt and MAP kinase pathways occur in virtually all UTC and those that can activate both pathways occur in the majority of UTC (Liu Z, Hou P, Ji M J, et al. Highly prevalent genetic alterations in receptor tyrosine kinases and PI3K/Akt and MAPK pathways in anaplastic thyroid cancers. *Cancer Res.* 2008). We functionally tested this hypothesis using NPA and KAT10 cells, which were poorly differentiated or undifferentiated cells derived from thyroid cancer, and both harbored BRAF mutation and PIK3CA amplifications.

The therapeutic potential of targeting the PI3K/Akt pathway has been previously tested in some cancers (Marone R, Cmiljanovic V, Giese B, Wymann M P. Targeting phosphoinositide 3-kinase-Moving towards therapy. *Biochim Biophys Acta.* 2007 Oct. 12; [Epub ahead of print]). Similarly, previous studies have also tested the therapeutic potential of targeting the MAP kinase pathway in some cancers (Kohno M, Pouyssegur J. Targeting the ERK signaling pathway in cancer therapy. *Ann Med.* 2006; 38:200-211; Sebolt-Leopold J S, Herrera R, Ohren J F. The mitogen-activated protein kinase pathway for molecular-targeted cancer treatment. *Recent Results Cancer Res.* 2007; 172:155-167). Consistent with these previous results in other cancers are our data in the present study demonstrating that suppression of either of the two pathways could cause significant inhibition of thyroid cancer cell proliferation and invasion, colony formation, and tumor growth. Our data were also consistent with the results in some recent in vitro and in vivo studies that targeted at one of the two signaling pathways with various pharmaceutical agents in thyroid cancer cells (Liu D, Hu S, Hou P, Jiang D, Condouris S, Xing M. Suppression of BRAF/MEK/MAP kinase pathway restores expression of iodide-metabolizing genes in thyroid cells expressing the V600E BRAF mutant. *Clin Cancer Res.* 2007a; 13:1341-1349; Liu D, Liu Z, Condouris S, Xing M. BRAF V600E maintains proliferation, transformation, and tumorigenicity of BRAF-mutant papillary thyroid cancer cells. *J Clin Endocrinol Metab.* 2007b; 92:2264-2271; Ouyang B, Knauf J A, Smith E P, et al. Inhibitors of Raf kinase activity block growth of thyroid cancer cells with RET/PTC or BRAF mutations in vitro and in vivo. *Clin Cancer Res.* 2006; 12:1785-1793; Salvatore G, De Falco V, Salerno P, et al. BRAF is a therapeutic target in aggressive thyroid carcinoma. *Clin Cancer Res.* 2006; 12:1623-1629; Liu D, Liu Z, Jiang D, Dackiw A P, Xing M. Inhibitory Effects of the Mitogen-Activated Protein Kinase Kinase Inhibitor CI-1040 on the Proliferation and Tumor Growth of Thyroid Cancer Cells with BRAF or RAS Mutations. *J Clin Endocrinol Metab.* 2007c; 92:4686-4695; Furuya F, Lu C, Willingham M C, Cheng S Y. (2007) Inhibition of phosphatidylinositol 3-kinase delays tumor progression and blocks metastatic spread in a mouse model of thyroid cancer. *Carcinogenesis.* 2007; 28:2451-2458).

In the present study, by specific knockdown using shRNA approaches we for the first time demonstrated the therapeutic potential of specifically targeting the PI3K/Akt pathway in thyroid cancer. The most striking and unique aspect of the present study, however, was the demonstration that dually targeting PI3K/Akt and MAP kinase pathways was more effective and, in many ways, synergistic in inhibiting thyroid cancer cells. This included, for example, the inhibition of thyroid cancer cell proliferation and invasion and, remarkably, the induction of cell apoptosis and thyroid iodide-metabolizing gene expression. It should be emphasized that inhibition of cell proliferation induced by suppression of a single pathway was mainly through cell cycle arrest at G0/G1 phase whereas dual suppression of the PI3K/Akt and MAP kinase pathways significantly or synergistically increased cell apoptosis. This result suggests that a therapeutic approach dually targeting the two pathways would be far more effective in killing thyroid cancer cells and may therefore be curative. This may explain some previous studies showing that individually targeting the PI3K/Akt or MAP kinase pathway seemed to only induce slow in vivo growth of thyroid cancer, but not elimination of the tumor, in mice (Liu D, Hu S, Hou P, Jiang D, Condouris S, Xing M. Suppression of BRAF/MEK/MAP kinase pathway restores expression of iodide-metabolizing genes in thyroid cells expressing the V600E BRAF mutant. *Clin Cancer Res.* 2007a; 13:1341-1349; Furuya F, Lu C, Willingham M C, Cheng S Y. (2007). Inhibition of phosphatidylinositol 3-kinase delays tumor progression and blocks metastatic spread in a mouse model of thyroid cancer. *Carcinogenesis.* 2007; 28:2451-2458). However, the interpretation of data on tumor in nude mice may need caution as the immune competency of nude mice may sometimes not be completely absent. Consequently, survival of human cancer cells in an immunologically unfavorable environment in nude mice could be more susceptibly affected by knockdown of either of the PI3K/Akt and MAP kinase pathways. This could partially account for the dramatic suppression of xenograft tumors derived from cells with shRNA knockdown of only one pathway in the present study. Nevertheless, it is convincing based on the present study that dually targeting the PI3K/Akt and MAP kinase pathways would be significantly more effective and, in fact, necessary in inhibiting, killing, and perhaps curing thyroid cancer in the human body.

Another unique and exciting finding in the present study was the synergistic effect of dual knockdown of the PI3K/Akt and MAP kinase pathways, compared with knockdown of either pathway alone, on the restoration of thyroid iodide-metabolizing gene expression. Several such genes could be robustly expressed with this approach in contrast with the limited expression of limited number of thyroid genes in human thyroid cancer cells demonstrated in previous studies targeting only the MAP kinase pathway (Liu D, Liu Z, Jiang D, Dackiw A P, Xing M. Inhibitory Effects of the Mitogen-Activated Protein Kinase Kinase Inhibitor CI-1040 on the Proliferation and Tumor Growth of Thyroid Cancer Cells with BRAF or RAS Mutations. *J Clin Endocrinol Metab.* 2007c; 92:4686-4695). As these molecules are classical differentiation markers of thyroid cells, their robust re-expression represents evidence that dually suppressing the PI3K/Akt and MAP kinase pathways can effectively promote re-differentiation of PDTC and UTC cells. More importantly, these results have strong clinical implications with respect to radioiodine ablation treatment for thyroid cancer. It is interesting to note that in the present study the most responsive gene to induction by suppressing the PI3K/Akt and MAP kinase pathways was the NIS gene. NIS plays a pivotal role in the uptake of iodide by thyroid cells. The robust expression of NIS gene was demonstrated at both mRNA and protein levels, the latter being abundantly transported to the cell membrane as demonstrated on our flow cytometric and immunoflorescent microscopic analyses. It is important to note that expression of these genes conferred thyroid cancer cells the functional ability to take up radioiodide. Thus, dual suppression of PI3K/Akt and MAP kinase pathways may restore the radioiodine avidity of PDTC and UTC and confer the responsiveness of these cancers to radioiodine treatment.

In summary, using specific inhibitors and shRNA knockdown approaches, we tested the therapeutic potential of dually targeting the PI3K/Akt and MAP kinase pathways in PDTC and UTC cells. Although individually targeting either pathway alone was previously tested in cancers, including thyroid cancer, the present study was the first to test the synergistic therapeutic effects of targeting both pathways in human cancers using shRNA approaches. This approach demonstrated remarkable inhibition of poorly differentiated and undifferentiated thyroid cancer cells and, more importantly, induction of cell apoptosis and robust thyroid gene expression with restoration of iodide uptake. Given the availability of several specific, potent and safe inhibitors of the PI3K/Akt and MAP kinase pathways (Kohno M, Pouyssegur J. Targeting the ERK signaling pathway in cancer therapy. *Ann Med.* 2006; 38:200-211; Marone R, Cmiljanovic V, Giese B, Wymann M P. Targeting phosphoinositide 3-kinase-Moving towards therapy. *Biochim Biophys Acta.* 2007 Oct. 12; [Epub ahead of print]; Sebolt-Leopold J S, Herrera R, Ohren J F. The mitogen-activated protein kinase pathway for molecular-targeted cancer treatment. *Recent Results Cancer Res.* 2007; 172:155-167), dually targeting the two pathways as a potentially effective therapeutic strategy for human cancers is clinically possible. This strategy may be particularly effective for PDTC and UTC in conjunction with radioiodine therapy conventionally used for thyroid cancer.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLES

Example 1

Synergistic/Additive Inhibition of Cell Proliferation and Induction of Thyroid Iodide-Handling Gene Expression in Melanoma Cells by Dually Suppressing the MAPK and PI3K/Akt Pathways Using Specific Inhibitors We first used the melanoma cell line NPA cell, a cell clone derived from the melanoma cell line M14 cell (35), and inhibitors of the MAPK and PI3K/Akt pathways to test the therapeutic potential for melanoma of dully targeting the two pathways to induce potent cell inhibition coupled with thyroid iodide-handling gene expression for potential radioiodide treatment. As shown in FIG. 1A, treatment of cells with the MEK inhibitor U0126 and the Akt inhibitor IV (Akti IV) (38) strongly inhibited phosphorylation of ERK (p-ERK) and Akt (p-Akt), respectively. Correspondingly, the two inhibitors inhibited cell proliferation partially when used individually and virtually completely when used in combination (FIG. 1B). To explore the ability of suppressing the MAPK and PI3K/Akt pathways to induce the expression of iodide-metabolizing genes in melanoma cells, we tested the effects of U0126 and Akti IV on NPA cells which had no or low basal expression of iodide-handling genes. As shown in FIG. 1C, expression of several iodide-handling genes, including NIS, TSHR, Tg, and TTF1, was induced or dramatically enhanced after treatment of cells with U0126 or Akti IV. Combined use of the two inhibitors showed synergistic/additive effects in promoting the expression of some of these genes (FIG. 1C). Similar effects of these inhibitors of the MAPK and PI3K/Akt pathways on cell inhibition and iodide-handling gene expression were seen in DRO cells, a cell clone derived from the melanoma cell line A375 cell (35) (data not shown).

Example 2

Figure 2A:
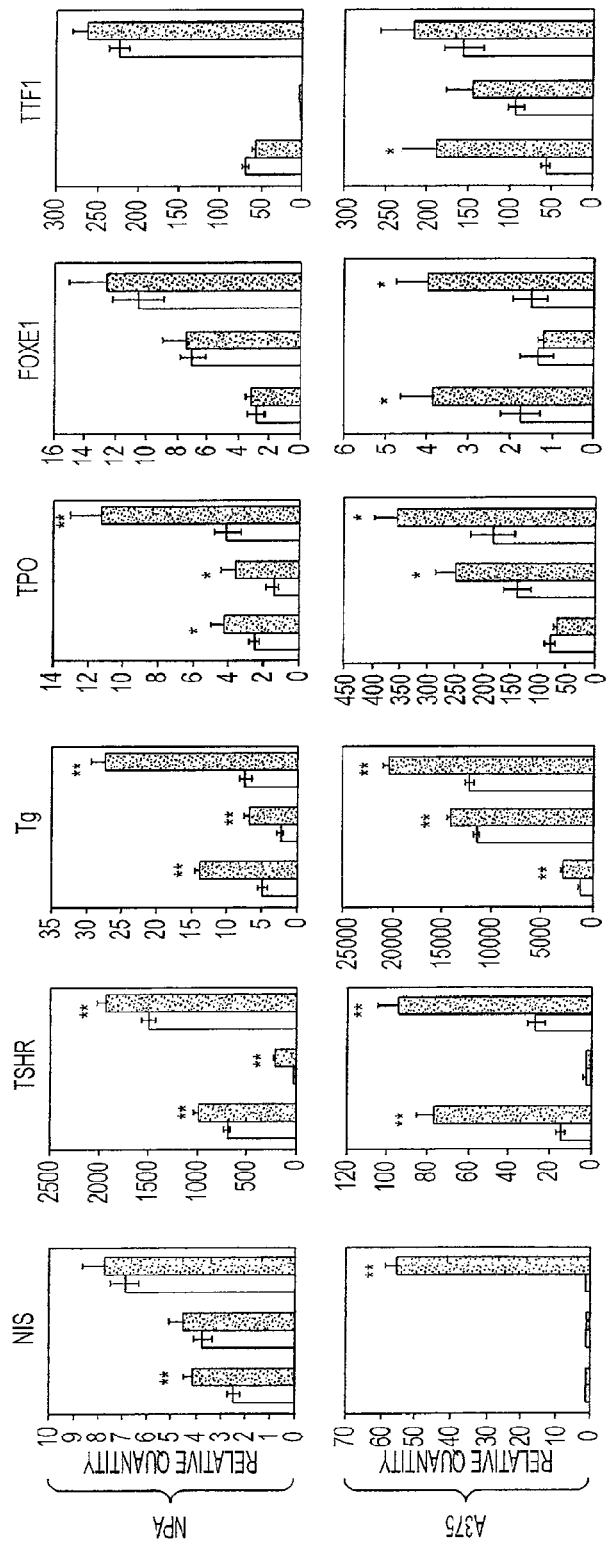
FIG. 2 Effect of TSH stimulation on expression of thyroid genes mediated by suppressing MAPK and PI3K/Akt pathways, individually or in combination, in melanoma cells (FIG. 2A: NPA and A375.
FIG. 2B: UACC62 and M14). Melanoma cells, as indicated, were treated with specific inhibitors (U0126 and Akti IV) as described in FIGS. 1A-1C. Before RNA was extracted, cells were treated with 40 mU/ml TSHb for 6 h. Details are described in the Materials and Methods. Data are presented as the mean±SD of values from three assays. In comparison with control, *, $P<0.05$; **, $P<0.01$.
Figure 2B:
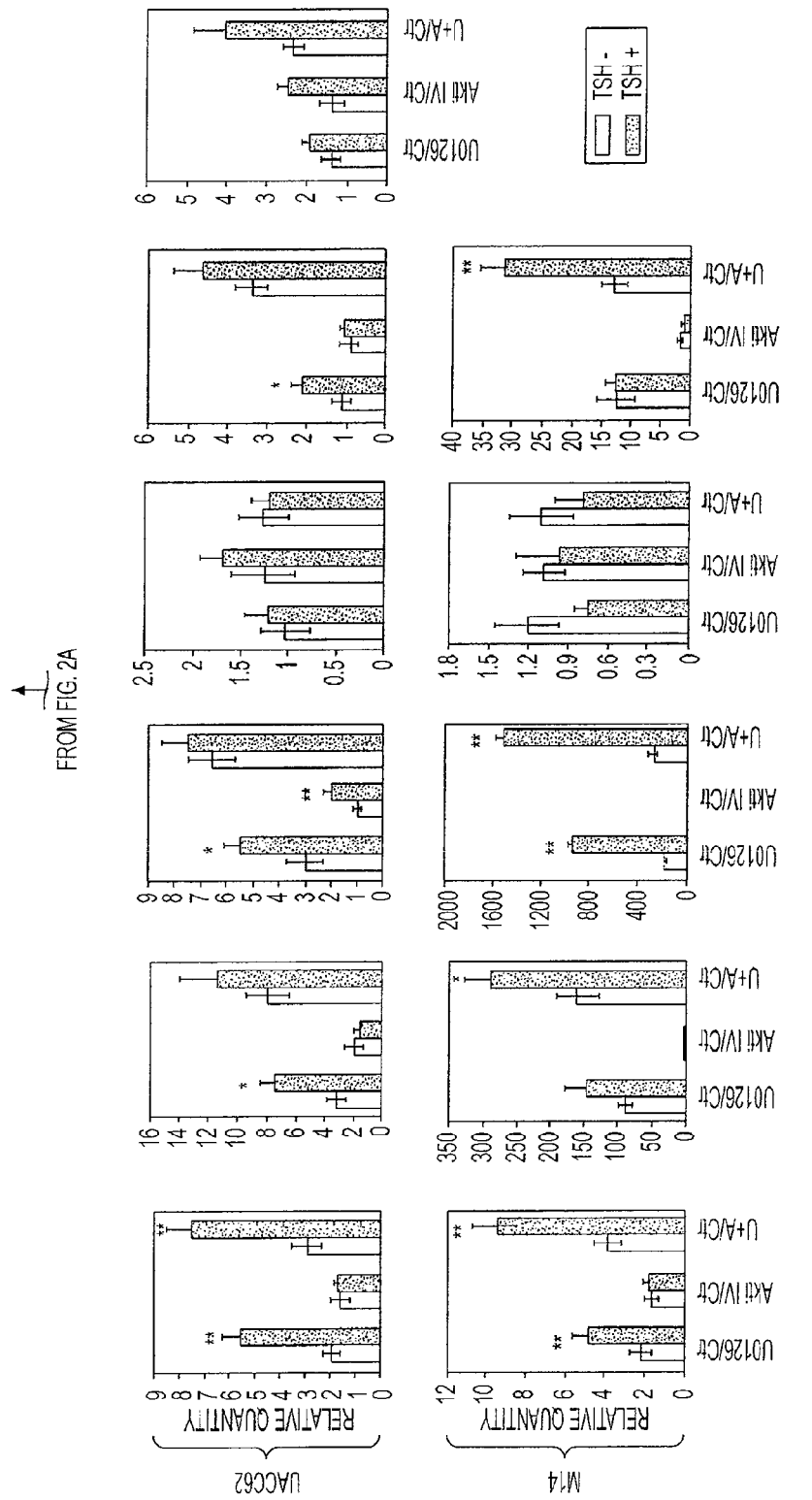

Expression of Iodide-Handling Genes in Various Melanoma Cell Lines Induced by Suppressing the MAPK and PI3K/Akt Pathways and its Enhancement or Synergy by TSH Stimulation Encouraged by the novel finding of the expression of iodide-handling genes upon suppression of the MAPK and PI3K/Akt pathways in the NPA cell, we extended this study to other melanoma cell lines. As shown in FIG. 2, in several melanoma cell lines tested, including M14, UACC62, A-375 and, again, NPA cells, dually suppressing the MAPK and PI3K/Akt pathways by U0126 and Akti IV showed synergistic/additive effects on the expression of most of the iodide-handling genes compared with suppressing either pathway alone. Since TSHR plays an important role in up-regulating the iodide-handling genes in thyroid cells (21) and is expressed in melanoma cells upon suppression of the MAPK and PI3K/Akt pathways, we investigated whether TSH treatment could affect the expression of iodide-handling genes in melanoma cells. Remarkably, treatment of melanoma cells with TSH enhanced or synergized the expression of many of the iodide-handling genes induced either by suppression of one signaling pathway alone or simultaneous suppression of both pathways (FIG. 2).

Example 3

Cellular Inhibition of Melanoma Cells by siRNA Knockdown of BRAF and Akt-1/2

Figure 3:
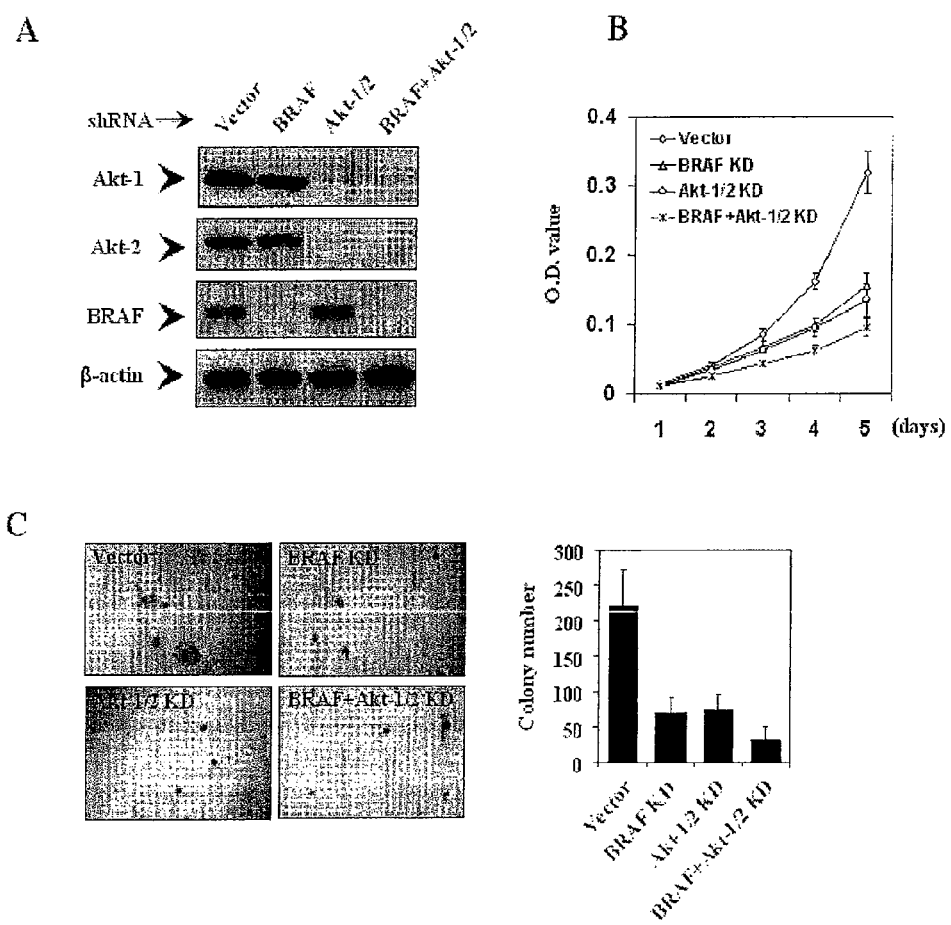
FIG. 3A-3C Effects of stable siRNA knockdown of BRAF and Akt-1/2, individually or dually, on cell proliferation and colony formation.
Figure 4:
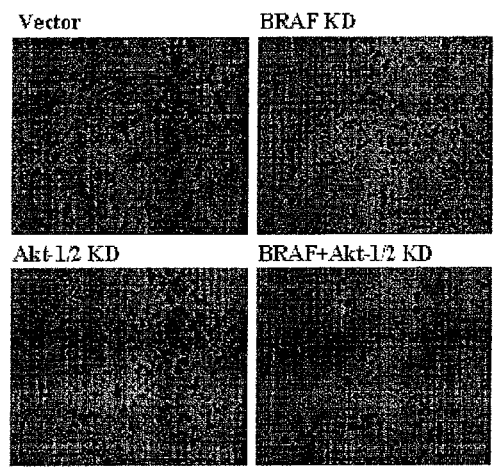
FIGS. 4A and 4B. Effects of stable siRNA knockdown of BRAF and Akt-1/2, individually or dually, on the invasion of NPA cells. Invading rate of cells stably transfected with specific siRNAs constructs to knock down BRAF and Akt-1/2, individually or dually, as described in FIGS. 3A-3C was measured using Matrigel-coated transwell cell culture chambers.
Figure 4:
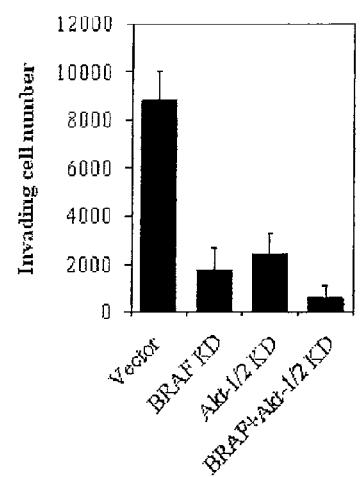

The above findings from the experiments using pharmacological inhibitors strongly suggest that dually targeting the MAPK and PI3K/Akt signaling pathways to induce both cellular inhibition and thyroid gene expression for adjunct radioiodine ablation therapy could be a novel and effective therapeutic strategy for melanoma. To more specifically test this hypothesis, in the next series of experiments, we used siRNA approaches to specifically knock down the MAPK and PI3K/Akt pathways, individually or dually in a selected melanoma cell line, the NPA cell. We pursued stable transfection with dual knockdown of Akt-1 and Akt-2 in combination with BRAF knockdown to achieve dual suppression of the two signaling pathways. To this end, we stably transfected NPA cells with pSicoR-PGK-euro encoding specific shRNA homologue sequences for Akt-1 and Akt-2 (Akt-1/2), superimposed with or without stable transfection of specific BRAF siRNA. Cells stably infected with lentivirus expressing BRAF and Akt-1/2 siRNA were successfully selected using puromycin, as demonstrated by effective suppression of expression of the corresponding proteins. Specifically, as shown in FIG. 3A, BRAF and Akt-1/2 siRNA stably and virtually completely inhibited the expression of BRAF and Akt-1/2, respectively, compared with empty vectors. As shown in FIGS. 3B and C, specific BRAF siRNA strongly inhibited proliferation and transformation of cells. Similarly, specific Akt-1/2 siRNA also exhibited dramatic inhibition of cell proliferation and transformation (FIGS. 3B and 3C). Further inhibition of cell proliferation and transformation was achieved by dual knockdown of BRAF and Akt-1/2 (FIGS. 3B and 3C). Migration/invasion of the NPA cells on Matrigel was also inhibited by stable siRNA knockdown of either pathway, with further inhibition achieved with dual knockdown of the two pathways (FIG. 4).

Example 4

Induction of $G_0/G_1$ Cell Cycle Arrest and Apoptosis by siRNA Knockdown of BRAF and Akt-1/2

Figure 5:
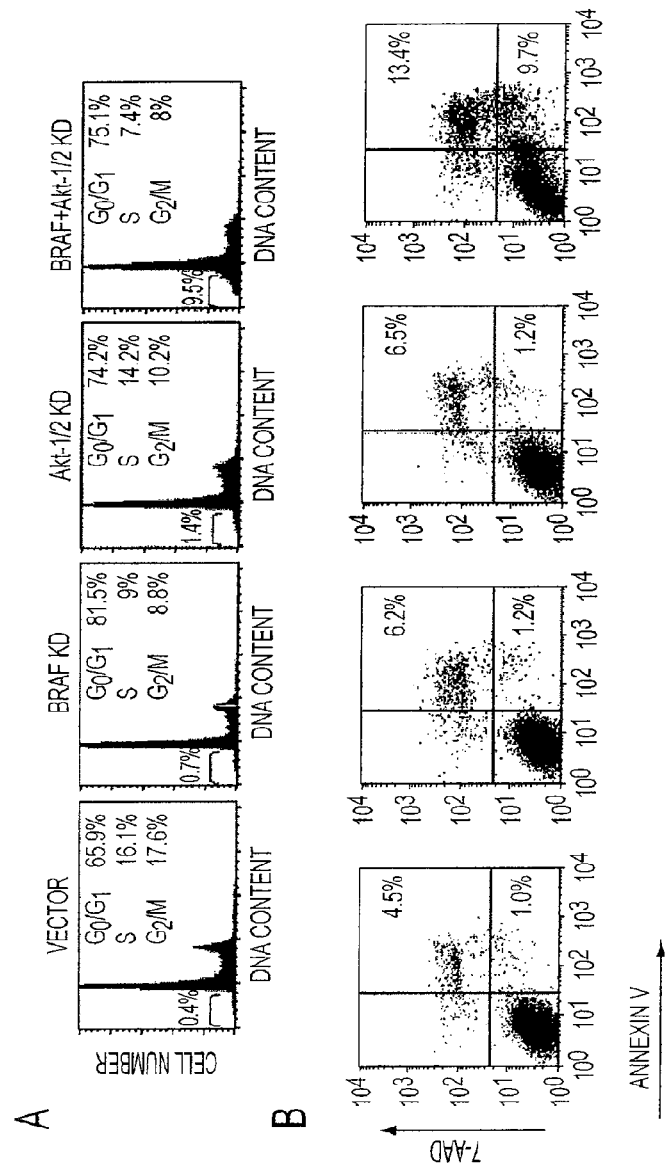
FIG. 5A-5B. Effects of siRNA knockdown of BRAF and Akt-1/2, individually or dually, on $G_0/G_1$ cell cycle arrest and apoptosis of NPA cells. NPA cells were transiently transfected with specific siRNAs to knock down BRAF and Akt-1/2, individually or dually as indicated. After a 4-day culture, DNA content (FIG. 5A) was measured by flow cytometry to determine cell cycle fractions. The fraction of apoptotic cells (sub-$G_0$) is indicated (FIG. 5A). Cell apoptosis (FIG. 5B) was measured by Annexin V staining and flow cytometry. The right lower quadrant of each plot contains early apoptotic cells, whereas the right upper quadrant contains late apoptotic cells. Details are described in the Materials and Methods.

To investigate further the cellular events involved in the inhibition of cell proliferation by dual suppression of MAPK and PI3K/Akt pathways, we transiently transfected BRAF and Akt-1/2 siRNA in NPA cells and measured cell cycle and apoptotic patterns by flow cytometric analysis of DNA content and Annexin V expression (FIG. 5). Compared with control vector, siRNA knockdown of BRAF and Akt-1/2 caused an increase in the $G_0/G_1$ fraction from 65.9% to 81.5% (by 23.7%) and to 74.2% (by 12.6%), respectively (FIG. 5A). With dual knockdown of BRAF and Akt-1/2, there was a dramatic synergistic increase in the sub-$G_0$ fraction in comparison with control vector or knockdown of BRAF or Akt-1/2 alone (9.5% vs. 0.4-1.4%), reflecting increased cell apoptosis, and the $G_0/G_1$ fraction was correspondingly only moderately increased. These data were consistent with the apoptotic patterns shown in FIG. 5B, which showed a dramatic increase in both early and late apoptosis (9.7% and 13.4%, respectively) with dual knockdown of BRAF and Akt-1/2. In contrast, knockdown of BRAF or Akt-1/2 alone had a much smaller effect on cell apoptosis. These data suggest that both increased $G_0/G_1$ cell cycle arrest and cell apoptosis were involved in the inhibition of NPA cell growth by suppression of MAPK and PI3K/Akt pathways. The effects were most significant with dual knockdown of the MAPK and PI3K/Akt pathways, particularly for cell apoptosis.

Example 5

Figure 6:
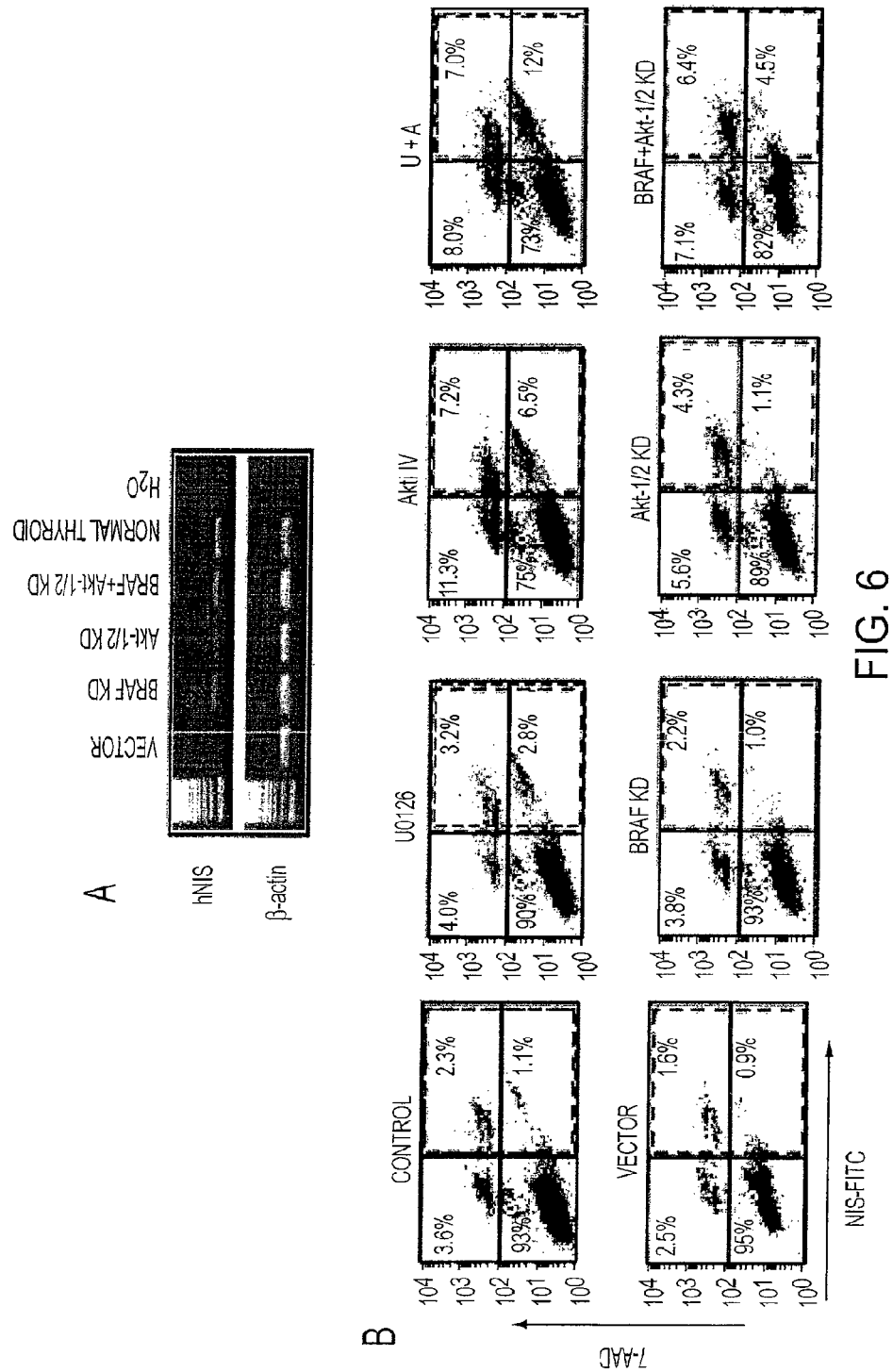
FIG. 6A-6D. Effects of suppression of MAPK and PI3K/Akt pathways, individually or in combination, on the expression of NIS and radioiodine uptake in NPA cells.
Figure 6:
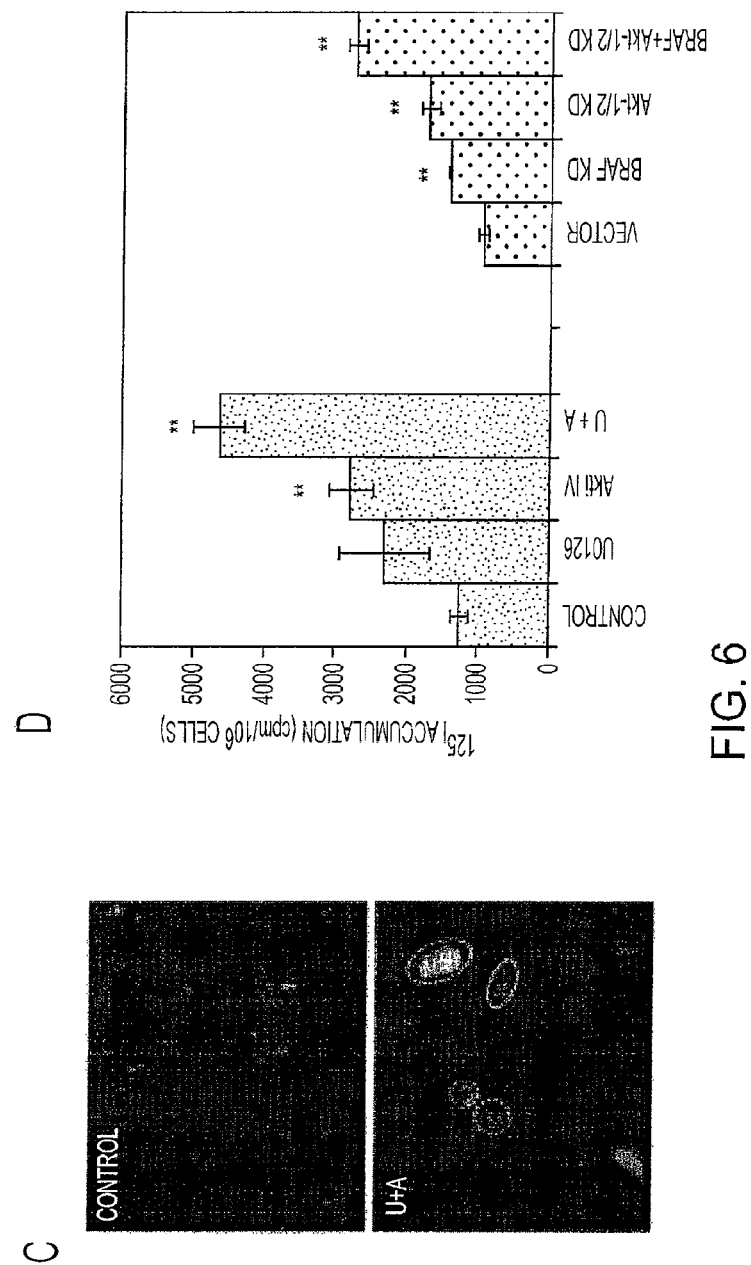

NIS Protein Expression and Radioiodide Uptake in Melanoma Cells Induced by Suppressing the MAPK and PI3K/Akt Pathways As NIS plays the most important role in cellular iodide uptake, we next explored further the effect of suppressing the MAPK and PI3K/Akt pathways on NIS expression in melanoma cells. As shown in FIG. 6A, stable knockdown of BRAF and/or Akt-1/2 with specific siRNA induced the expression of NIS in NPA cells, consistent with the results achieved with treatments of cells with pharmacological inhibitors (FIG. 1C and FIG. 2). We next investigated the effects of suppressing the MAPK and PI3K/Akt pathways on the expression of NIS protein in NPA cells. As shown in FIG. 6B, U0126 and Akti IV increased the NIS expression from 3.4% to 6% and 13.7%, respectively, and to 19% with combination of the two (FIG. 6B, upper panel). Although both U0126 and Akti IV induced NIS protein expression, Akti IV showed a more pronounced effect (FIG. 6B, upper panel). Combination of U0126 and Akti IV showed significantly enhanced or synergized effects on NIS protein expression (FIG. 6B, upper panel). Similarly, siRNA knockdown of BRAF and Akt-1/2 could each increase the NIS protein expression, albeit modestly, and dual knockdown of BRAF and Akt-1/2 showed enhanced effects (FIG. 6B, lower panel). We also performed immunofluorescent microscopy, which showed that dual inhibition of the MAPK and PI3K/Akt pathways by U0126 and Akti IV robustly induced the expression of NIS protein on cell membranes (FIG. 6C).

Given the induction of expression of iodide-handling genes in melanoma cells by suppression of the MAPK and PI3K/Akt pathways, we finally examined functionally the ability of these cells to take up radioiodide. As shown in FIG. 6D, treatment of NPA cells with U0126 or Akti IV significantly increased radioiodide uptake and combination of the two inhibitors resulted in an enhanced uptake. Stable knockdown of BRAF or Akt-1/2 could also increase radioiodide uptake, which was enhanced by simultaneous knockdown of the two.

Example 6 for Ex. 1-5

Materials and Methods

Human Melanoma Cell Lines and Cell Culture

The melanoma cell line UACC62 was obtained from the National Cancer Institute (NCI); melanoma cells lines M14 and A375 were obtained from American Type Culture Collection (ATCC). The NPA cell was provided by Dr. Guy J. F. Juillard (University of California-Los Angeles School of Medicine, Los Angeles, Calif.). This cell was previously mistakenly labeled as a thyroid cancer cell line (34) and has now been demonstrated to be a clone derived from the melanoma cell line M14 (35). NPA, M14 and UACC62 cells harbor genetic alterations that can activate both the MAPK and PI3K/Akt pathways: BRAF V600E mutation and PIK3CA amplifications in NPA and M14 cells, and BRAF V600E mutation and inactivating PTEN mutations (homozygous) in UACC62 cells. A375 harbors BRAF V600E mutation. Cells were cultured similarly as previously described (34,36). In some experiments as indicated, cells were additionally treated with bovine TSH (TSHβ) (Sigma) to test its effect on gene expression.

Western Blotting Assay.

Cells were lysed in RIPA buffer. Cellular proteins were resolved by electrophoresis on a SDS-polyacrylamide (10%) gel (SDS-PAGE), transferred onto PVDF membranes (Amersham Pharmacia Biotech, Piscataway, N.J.), and immunoblotted with specific primary antibodies. Anti-BRAF (Sc-166), anti-phospho-AKT (Sc-7985-R), anti-phospho-ERK (Sc-7383), and anti-Actin (Sc-1616-R) were purchased from Santa Cruz (Santa Cruz, Calif.). Anti-Akt-1 (#2967) and anti-Akt-2 (#2964) were purchased from Cell Signaling Technologies, Inc. (Beverly, Mass.). Antigen-antibody complexes were visualized using HRP-conjugated anti-mouse (Sc-2005, Santa Cruz, Calif.) or anti-rabbit (Sc-2004, Santa Cruz, Calif.) IgG antibodies and ECL Western Blotting Analysis System (Amersham Pharmacia).

RNA Extraction, RT-PCR Analysis, and Quantitative RT-PCR Analysis.

Total RNA was isolated using TRIzol reagent according to the instructions of the manufacturer (Invitrogen). Normal human thyroid RNA samples purchased from Stratagene (La Jolla, Calif.) were used as a positive control. The reverse transcription synthesis of cDNA was conducted with the SuperScript First-Strand Synthesis kit (Invitrogen). Conventional RT-PCR amplification was carried out to amplify NIS, TSHR, Tg, TPO, PAX8, FOXE1, and TTF1. The β-actin gene was run in parallel for quality control. The primer sequences were presented in Table 1. PCR products were resolved by 1.5% agarose gel electrophoresis and visualized by ethidium bromide staining Quantitative RT-PCR analysis was performed to evaluate expression of thyroid genes on an ABI Prism 7900HT Sequence Detector (Applied Biosystems), using SYBR Green PCR Core Reagents kit according to the instructions of the manufacturer (Applied Biosystems). The expression value of each gene was normalized to β-actin cDNA to calculate the relative amount of RNA present in each sample. The primers of intron-spanning thyroid-specific genes, NIS, TSHR, Tg, TPO, PAX8, FOXE1, and TTF1 were designed using Primer Express (Applied Biosystems, CA) and presented in Table 2.

TABLE 1

Hairpin RNA sequences used to specifically knock down BRAF, Akt-1 and -2

| Genes | Forward sequence (5'→3') | Reverse sequence (5'→3') |
|---|---|---|
| BRAF | TGCATCAATGGATACCGTT ATTCAAGAGATAACGGTA TCCATTGATGCTTTTTTC (SEQ ID NO: 5) | TCGAGAAAAAAGCATCAATG GATACCGTTATCTCTTGAAT AACGGTATCCATTGATGCA (SEQ ID NO: 7) |
| Akt-1/2 | TGTGGTCATGTACGAGATG ATTCAAGAGATCATCTCG TACATGACCACTTTTTTC (SEQ ID NO: 6) | TCGAGAAAAAAGTGGTCATG TACGAGATGATCTCTTGAAT CATCTCGTACATGACCACA (SEQ ID NO: 8) |

TABLE 2

Primer sequences used in RT-PCR analysis of the expression of thyroid iodide-handling genes

| Genes | Forward primer (5'→3') | Reverse primer (5'→3') | Product length |
|---|---|---|---|
| NIS | CTATGGCCTC AAGTTCCTCT (SEQ ID NO: 9) | TCGTGGCTAC AATGTACTGC (SEQ ID NO: 17) | 179 bp |
| TSHR | ATCAGGAGGA GGACTTCAGA (SEQ ID NO: 10) | TTTGAGGGCA TCAGGGTCTA (SEQ ID NO: 18) | 274 bp |
| Tg | GCAAAGGCTG TGAAGCAATT (SEQ ID NO: 11) | TGATAAAGTA GTCCCGGGTG (SEQ ID NO: 19) | 211 bp |
| TPO | CATTGGGAAG CAGATGAAGG (SEQ ID NO: 12) | TGTTGTCACA GATGACCCGA (SEQ ID NO: 20) | 128 bp |
| PAX8 | CAGGCATGGT GGCAGGAAGT (SEQ ID NO: 13) | ACAGATGGTC AAAGGCCGTG (SEQ ID NO: 21) | 177 bp |
| FOXE1 | GCTGGTTTTC CCTGTCTCTG (SEQ ID NO: 14) | AGATGGGGA GACTGAAGGT (SEQ ID NO: 22) | 100 bp |
| TTF1 | TACTGCAACG GCAACCTGGG (SEQ ID NO: 15) | GGCCATGTTC TTGCTCACGT (SEQ ID NO: 23) | 207 bp |
| β-Actin | TCTACAATGA GCTGCGTGTG (SEQ ID NO: 16) | TAGATGGGCA CAGTGTGGGT (SEQ ID NO: 24) | 228 bp |

Lentivirus-Mediated RNA Interference of BRAF, Akt-1, and Akt-2.

The lentiviral pSicoR-PGK-puro vectors (Addgene Inc. Cambridge, Mass., USA) encoding hairpin RNA sequences were used to knock-down BRAF and specific Aid isoforms. The hairpin sequences used for BRAF and combined Aid-1 and Akt-2 (Akt-1/2) were presented in Table 3. To generate lentiviral particles, human embryonic kidney 293 cells (ATCC, Manassas, Va., USA) were co-transfected with the lentiviral vector and compatible packaging plasmid mixture using Lipofectamine 2000 (Invitrogen), following the manufacturer's instructions. Melanoma cells were exposed to lentivirus-containing supernatant for 16 hours in the presence of Polybrene (Sigma). After 3-4 days, the cells were serum-starved (0.5% FBS) and harvested 24 hours later in RIPA lysis buffer (Santa Cruz, Calif.). Western blotting assays were used to detect the protein expression of BRAF, Akt-1, and Akt-2.

TABLE 3

Primer sequences used for quantitative RT-PCR analysis of the expression of thyroid iodide-handling genes

| Genes | Forward primer (5'→3') | Reverse primer (5'→3') | Product length |
|---|---|---|---|
| NIS | CCTGCTAACG ACTCCAGCA (SEQ ID NO: 25) | CCAGGGCACC GTAATAGAGA (SEQ ID NO: 33) | 106 bp |
| TSHR | GATATTCAAC GCATCCCCAG (SEQ ID NO: 26) | AGCTGCTGCA GAGTCACATC (SEQ ID NO: 34) | 149 bp |
| Tg | CACCAACTCC CAACTTTTCC (SEQ ID NO: 27) | CAACTGACCT CCTTTGCCA (SEQ ID NO: 35) | 123 bp |
| TPO | ACTTGGATCT CCATGTCGCT (SEQ ID NO: 28) | GCAGTGTGGA TTTAGTGCCA (SEQ ID NO: 36) | 106 bp |
| PAX8 | TGCCTCACAA CTCCATCAGA (SEQ ID NO: 29) | CAGGTCTACG ATGCGCTG (SEQ ID NO: 37) | 110 bp |
| FOXE1 | GCTGGTTTTC CCTGTCTCTG (SEQ ID NO: 30) | AGATGGGGAG ACTGAAGGT (SEQ ID NO: 38) | 100 bp |
| TTF1 | ACCAGGACAC CATGAGGAAC (SEQ ID NO: 31) | GCTCATGTTCA TGCCGCT (SEQ ID NO: 39) | 116 bp |
| β-Actin | GCACAGAGCC TCGCCTT (SEQ ID NO: 32) | GTTGTCGACGA CGAGCG (SEQ ID NO: 40) | 93 bp |

Cell Proliferation Assay.

Cells (800/well) were seeded into 96-well plates and cultured with 2.5% FBS. MTT assay was performed daily over a 5-day time course to evaluate cell numbers using a MTT cell proliferation assay kit (ATCC, Manassas, Va., USA) following the manufacturer's instructions.

Colony Formation Assay.

For soft-agar colony-formation assay, $1 \times 10^5$ cells were plated into 6-well plates with a bottom layer of 0.6% agar and a top layer of 0.3% agar. Following the hardening of soft agar, plates were incubated at 37° C. with 5% $CO_2$. After 2-3 weeks of culture, colonies were counted and photographed under a microscope.

Cell Invasion Assay.

Cell invasion was assayed in triplicates using Matrigel-coated Transwell cell culture chambers (#354481, BD Biosciences). Briefly, cells ($1.5 \times 10^5$ cells/well) suspended in serum-free medium were placed in the upper chamber of the Transwell insert, and RPMI 1640 medium containing 10% FBS was added to the lower chamber. Following a 24 h-incubation at 37° C. with 5% $CO_2$, non-invasive cells in the upper chamber were removed and invasive cells were fixed in 100% methanol and stained with 0.5% crystal violet in 2% ethanol. The numbers of invasive cells were counted and photographed.

Cell Cycle Analysis.

Cells were harvested, washed twice in PBS, and resuspended in 70% ethanol on ice for at least 30 min. After centrifugation, $1\times10^6$ cells transiently transected with various siRNA constructs were resuspended in 1 ml of propidium iodide staining solution (50 μg of propidium iodide, 1 mg of RNase A, and 1 mg of glucose per 1 ml PBS) and incubated at room temperature for 30 min. Cell cycles were analyzed based on DNA contents by FACS using a LSR Flow Cytometer (BD Biosciences, NJ).

Apoptosis Assay.

Cells were transiently transfected with various siRNA constructs. After a 24-h serum starvation, cells were harvested, washed with PBS, and subjected to sequential staining with Annexin V-PE Apoptosis Detection Kit (BD Biosciences) by two-color flow cytometry, according to the manufacturer's protocol. Cells that were Annexin V-positive and 7-AAD-negative served as early apoptotic population. Cells that were both Annexin V- and 7-AAD-positive served as late apoptotic population.

Flow Cytometry Analysis of NIS Expression.

Cells treated with specific inhibitors and various siRNA constructs to induce the expression of NIS were incubated with VJ2 α-hNIS mAb (a gift from Dr. Sabine Costagliola at the Free University of Brussels) (37) diluted at 1:20 in FACS buffer (3% FBS, 0.02% $NaN_3$ in PBS) at 4° C. for 1 h. Cells were then washed once with FACS buffer and incubated with FITC-conjugated α-mouse IgG (Sigma) diluted at 1:100 in FACS buffer at 4° C. for 1 h. Cells were washed again in FACS buffer, resuspended in 2 ml of FACS buffer with 7-AAD, and analyzed by FACS using a LSR Flow Cytometer (BD Biosciences, NJ). Secondary antibody alone was used as a negative control. Fluorescent microscopic examination was conducted to monitor NIS expression (Nikon Corporation, Tokyo, Japan).

Radioactive Iodine Uptake Assay.

Cells ($1\times10^6$ cells/well) treated under the indicated conditions were seeded in 12-well plates. Cells in 0.5 ml/well were incubated with RPMI 1640 medium containing 1 μCi $Na^{125}I$ and 5 μM non-radioactive NaI for 1 h at 37° C. with 5% $CO_2$. The medium was subsequently aspirated and cells were quickly washed twice with ice-cold Hank's balanced salt solution (HBSS) and harvested with tripsin-EDTA. Cells were collected and radioactivity was counted by a gamma-counter.

Statistical Analysis.

All the experiments were similarly done at least three times. The statistical significance of differences between two groups of data was analyzed by paried t-test and a P value of <0.05 was considered significant.

Example 7

Figure 7:
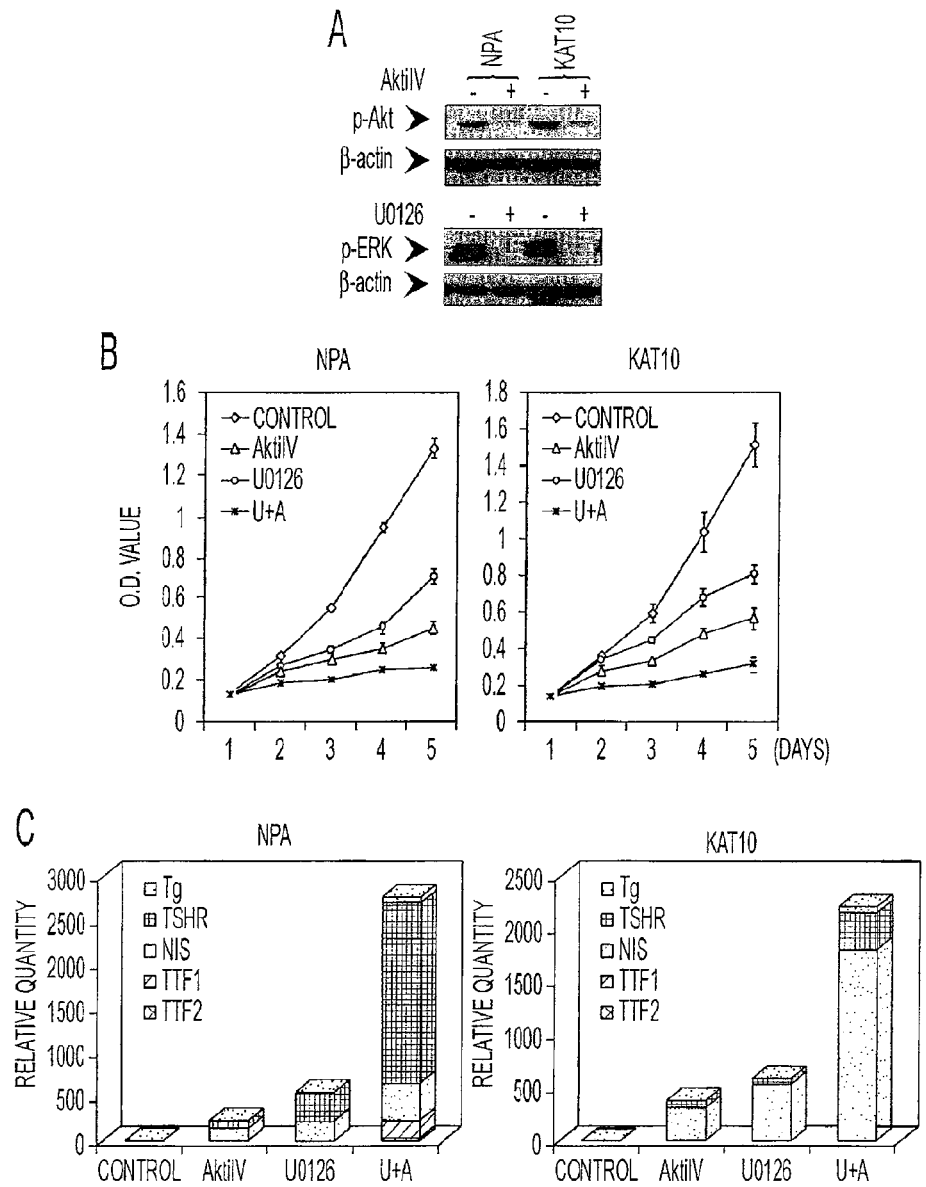
FIG. 7 A) Inhibition of Akt and ERK phosphorylation by suppression of PI3K/Akt and MAP kinase pathways using the Akt-specific inhibitor Akti IV and the MEK-specific inhibitor U0126, respectively. NPA and KAT10 cells were treated with Akti IV at 0.5 and 2 µM, respectively, or with U0126 at 10 µM for 30 h. Cells were lysed for Western blotting assay. The activities of PI3K/Akt and MAP kinase pathways were reflected by the level of phosphorylated Akt and ERK detected with specific anti-phosphorylated Akt (p-Akt) and anti-phosphorylated ERK (p-ERK) antibodies. Immunoblotting with antibody against β-actin was used for quality control.

Inhibition of Cell Proliferation and Restoration of Iodide-Metabolizing Gene Expression in Thyroid Cancer Cells by Dually Suppressing the PI3K/Akt and MAP Kinase Pathways Using Specific Inhibitors As the first step to explore the therapeutic potential of dully targeting the PI3K/Akt and MAP kinase pathways, we tested the effects of specific inhibitors of the two pathways in thyroid cancer cell lines NPA and KAT10 cells, which were poorly differentiated or undifferentiated and harbored activating genetic alterations in both PI3K/Akt and MAP kinase pathways. As shown in FIG. 7A, the Akt inhibitor IV (Akti IV) and the MEK inhibitor U0126 strongly inhibited phosphorylation of Akt (p-Akt) and ERK (p-ERK), respectively, in both cells. Correspondingly, the two inhibitors inhibited cell proliferation partially when used individually and virtually completely when used in combination in both cells (FIG. 7B). To explore the role of PI3K/Akt and MAP kinase pathways in the expression of thyroid iodide-metabolizing genes, we tested the effects of Akti IV and U0126 on NPA and KAT10 cells which virtually had no or very low basal expression of most of the iodide-metabolizing genes. As shown in FIG. 7C, expression of several thyroid genes, including Tg, TSHR, NIS, and TTF1, was restored after treatment of the cells with Akti IV or U0126. Remarkably, combined use of the two inhibitors showed a dramatic synergistic effect in promoting the re-expression of these genes, particularly Tg, TSHR, and NIS (FIG. 7C). Similar effects of these inhibitors of the PI3K/Akt and MAP kinase pathways on cell inhibition and thyroid gene re-expression were seen in KAK1, KAT5, KAT7, ARO and C643 thyroid cancer cell lines (data not shown). TPO and PAX8 genes were naturally robustly expressed in these cells (data not shown) and were therefore not investigated in the present study.

Example 8

Figure 8:
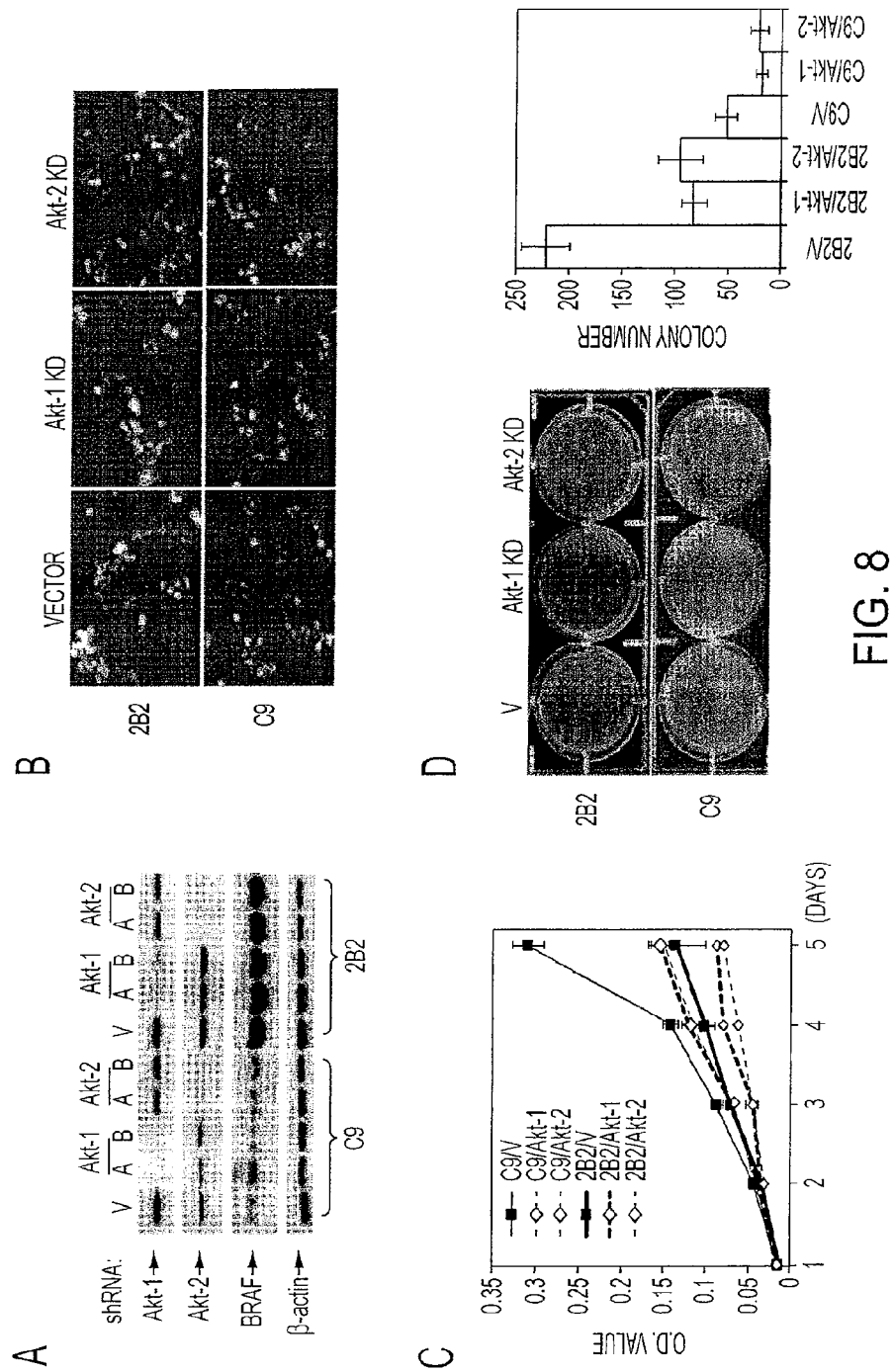
FIG. 8A-8D. Effects of transient isoform-specific knockdown of Akt by siRNA on proliferation and colony formation of thyroid cancer cells additionally transfected with or without specific siRNA for BRAF.

Inhibition of Cell Proliferation and Transformation by siRNA Knockdown of Akt-1, Akt-2, and BRAF Given these encouraging data on pharmacological inhibitors in thyroid cancer cells, we took the next steps to specifically explore the therapeutic potential of interfering with PI3K/Akt and MAP kinase pathways in thyroid cancer using specific siRNA approaches. Among the several isoforms of Akt, Akt-1 and Akt-2 were shown to be particularly abundant and important in thyroid cancer (Ringel M D, Hayre N, Saito J, et al. Overexpression and overactivation of Akt in thyroid carcinoma. *Cancer Res.* 2001; 61:6105-6111). We therefore first examined the individual role of Akt-1 or Akt-2 using transient siRNA transfection to individually knock down the two Akts. To this end, we used KAT10 cells to perform siRNA transfection using the lentiviral vector pSicoR-PGK-GFP that encoded short hairpin RNA (shRNA) sequences to specifically down-regulate the expression of Akt-1 or Akt-2. To dually interfere with the PI3K/Akt and MAP kinase pathways, KAT10 cell clones stably transfected with BRAF-specific siRNA (clone C9) or control scrambled siRNA (clone 2B2) that had been previously established (Liu D, Hu S, Hou P, Jiang D, Condouris S, Xing M. Suppression of BRAF/MEK/MAP kinase pathway restores expression of iodide-metabolizing genes in thyroid cells expressing the V600E BRAF mutant. *Clin Cancer Res.* 2007a; 13:1341-1349; Liu D, Liu Z, Condouris S, Xing M. BRAF V600E maintains proliferation, transformation, and tumorigenicity of BRAF-mutant papillary thyroid cancer cells. *J Clin Endocrinol Metab.* 2007b; 92:2264-2271) were used for superimposed transfection with Akt-1 or Akt-2 siRNA. As shown in FIG. 8A, specific Akt-1, Akt-2 and BRAF siRNA virtually completely suppressed the expression of their corresponding proteins. This high efficiency of transfection with the pSicoR-PGK-GFP vector was also confirmed by the persistent expression of the tag GFP even at 2 weeks on fluorescent microscopy (FIG. 8B). Knockdown of either Akt-1 or Akt-2 had a significant inhibitory effect on thyroid cancer cell proliferation (FIG. 8C) and colony formation on soft agar (representing cell transformation) (FIG. 8D). Compared with BRAF control siRNA (2B2/V), knockdown of BRAF (C9/V) also had a significant inhibitory effect on cell proliferation and colony formation (FIGS. 8C and 8D) as demonstrated previously (Liu, supra). Combinational knockdown of Akt-1 or Akt-2 with BRAF caused a further inhibition of thyroid cancer cell proliferation and colony formation (FIGS. 8C and 8D).

Figure 9:
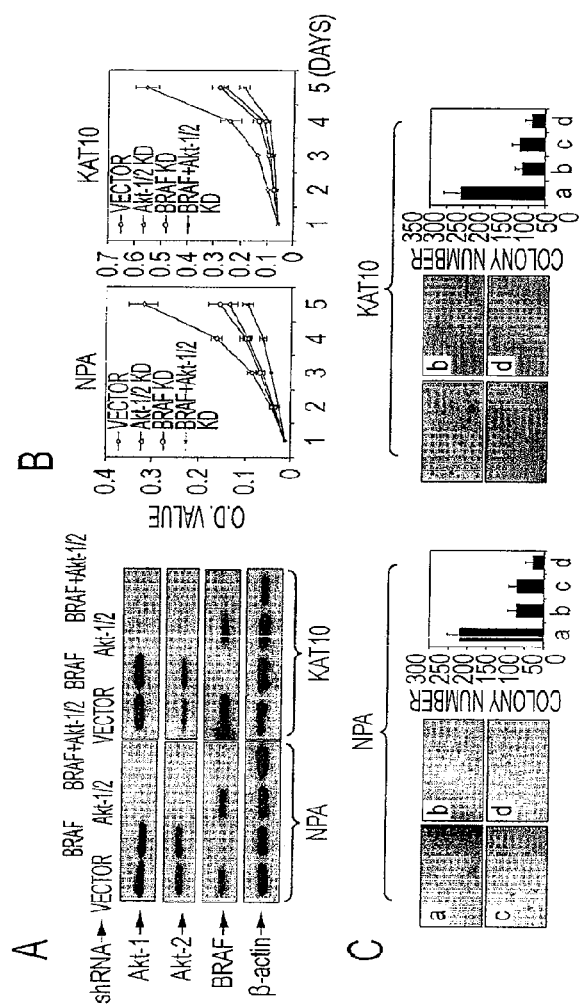
FIG. 9A-9C. Effects of stable siRNA knockdown of Akt-1/2 and BRAF, individually or dually, on thyroid cancer cell proliferation and colony formation.

These data suggested that Akt-1 and Akt-2 individually played a significant but partial role in thyroid cancer cell growth. Based on these data from transient siRNA transfection, we next pursued stable transfection with dual knockdown of Akt-1 and Akt-2 in combination with BRAF knockdown to achieve maximal dual suppression of PI3K/Akt and MAP kinase signalings. To this end, we stably transfected NPA and KAT10 cells with pSicoR-PGK-puro encoding specific shRNA homologue sequences for Akt-1 and Akt-2 (Akt-1/2), superimposed with or without stable transfection of specific BRAF siRNA. Thyroid cancer cells stably infected with lentivirus expressing Akt-1/2 and BRAF siRNA were successfully selected using puromycin, as demonstrated by effective suppression of expression of the corresponding proteins. Specifically, as shown in FIG. 9A, Akt-1/2 and BRAF siRNA stably and virtually completely inhibited the expression of Akt-1/2 and BRAF, respectively, in both NPA and KAT10 cells compared with empty vectors. As seen with the pSicoR-PGK-GFP system (FIG. 8), stable BRAF siRNA transfection with the pSicoR-PGK-puro system strongly inhibited cell proliferation and transformation of both NPA and KAT10 cells (FIGS. 9B and 9C). Similarly, specific Akt-1/2 siRNA also exhibited dramatic inhibition of thyroid cancer cell proliferation and transformation (FIGS. 9B and 9C). Significant further inhibition of cell proliferation and transformation was achieved by dual knockdown of Akt-1/2 and BRAF (FIGS. 9B and 9C). These stable transfectants were used in most of the following experiments to further explore the therapeutic potential of dually targeting both PI3K/Akt and MAP kinase pathways in thyroid cancer cells.

Example 9

Inhibition of Cell Invasion by Stable siRNA Knockdown of Akt-1/2 and BRAF

Figure 10:
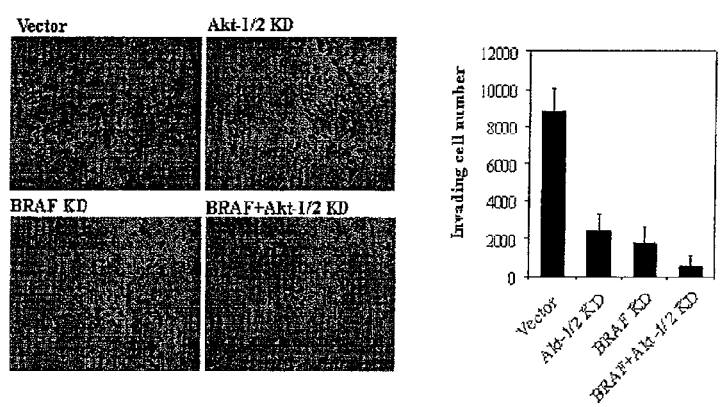
FIG. 10A-10B. Effects of stable siRNA knockdown of Akt-1/2 and BRAF, individually or dually, on the invasion of thyroid cancer cells. Invading rate of cells stably transfected with specific siRNAs constructs to knock down Akt-1/2 and BRAF, individually or dually, as described in FIG. 3 was measured using Matrigel-coated transwell cell culture chambers. Shown are representative results of invasive NPA (FIG. 10A) and KAT 10 (FIG. 10B) cells. The bar graphs in the right panels, corresponding to left panels, show means±SD of the numbers of invading cells from three independent experiments.
Figure 10:
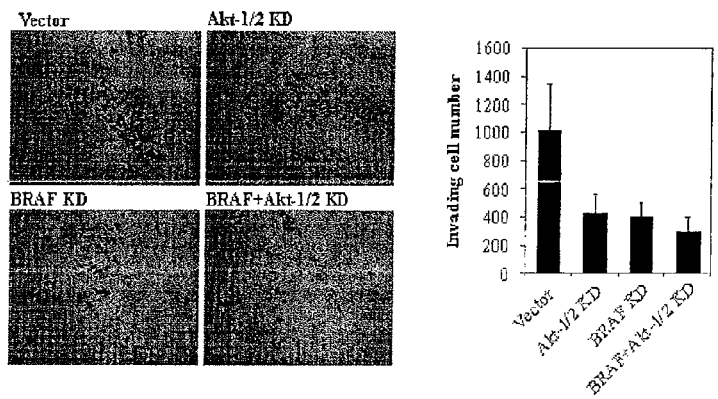

To investigate whether suppression of PI3K/Akt and MAP kinase pathways could suppress invasion of thyroid cancer cells, we performed Matrigel invasion assay on NPA and KAT10 cells stably expressing Akt-1/2 and BRAF siRNA. As shown in FIG. 10, the number of invading cells was strongly inhibited with knockdown of Akt-1/2 or BRAF compared with empty vector. Dual siRNA knockdown of Akt-1/2 and BRAF caused further inhibition of cell invasion, particularly in NPA cells (FIG. 10).

Example 10

Figure 11:
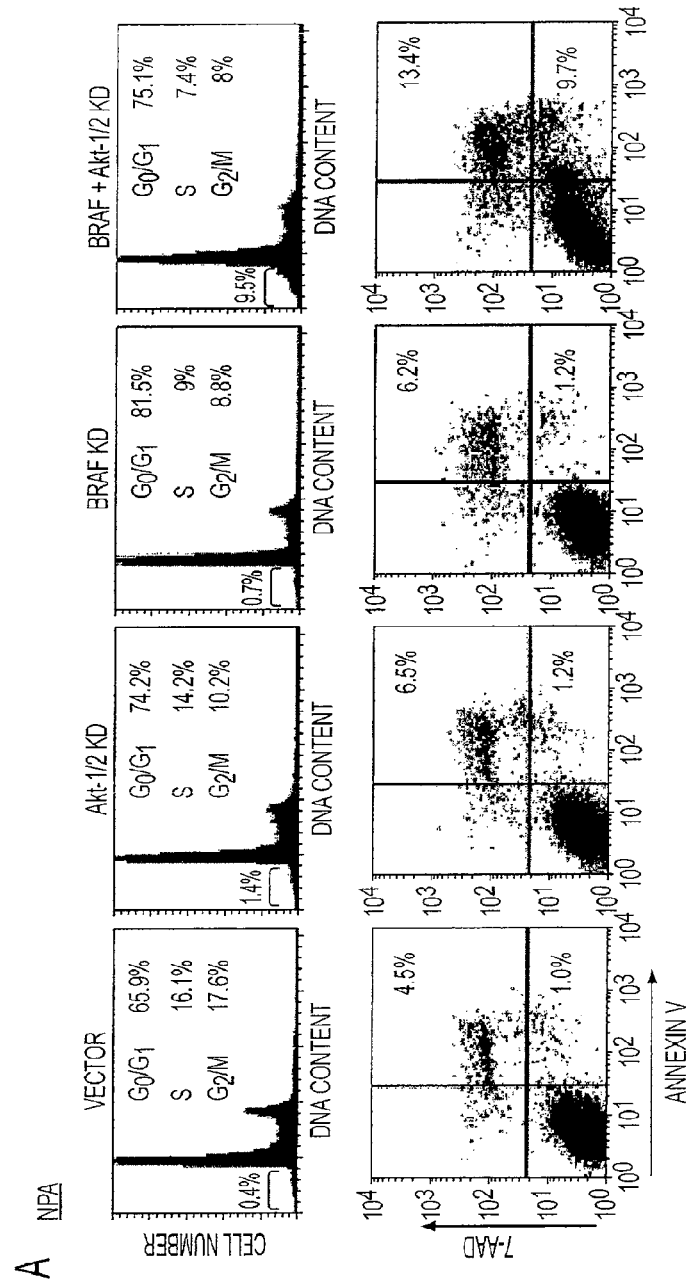
FIG. 11A-11B. Effects of siRNA knockdown of Akt-1/2 and BRAF, individually or dually, on G0/G1 cell cycle arrest and apoptosis of thyroid cancer cells. NPA (FIG. 11A) and KAT10 (B) cells were transiently transfected with specific siRNAs to knock down Akt-1/2 and BRAF, individually or dually as indicated. After a 4-day culture, DNA content (FIG. 11A and FIG. 11B, upper panels) was measured by flow cytometry to determine cell cycle fractions. The fraction of apoptotic cells (sub-G0) is indicated (A, upper panel). Cell apoptosis (FIG. 11A and FIG. 11B, lower panels) was measured by Annexin V staining and flow cytometry. The right lower quadrant of each plot contains early apoptotic cells, whereas the right upper quadrant contains late apoptotic cells. Details are described in the Experimental Procedures.
Figure 11:
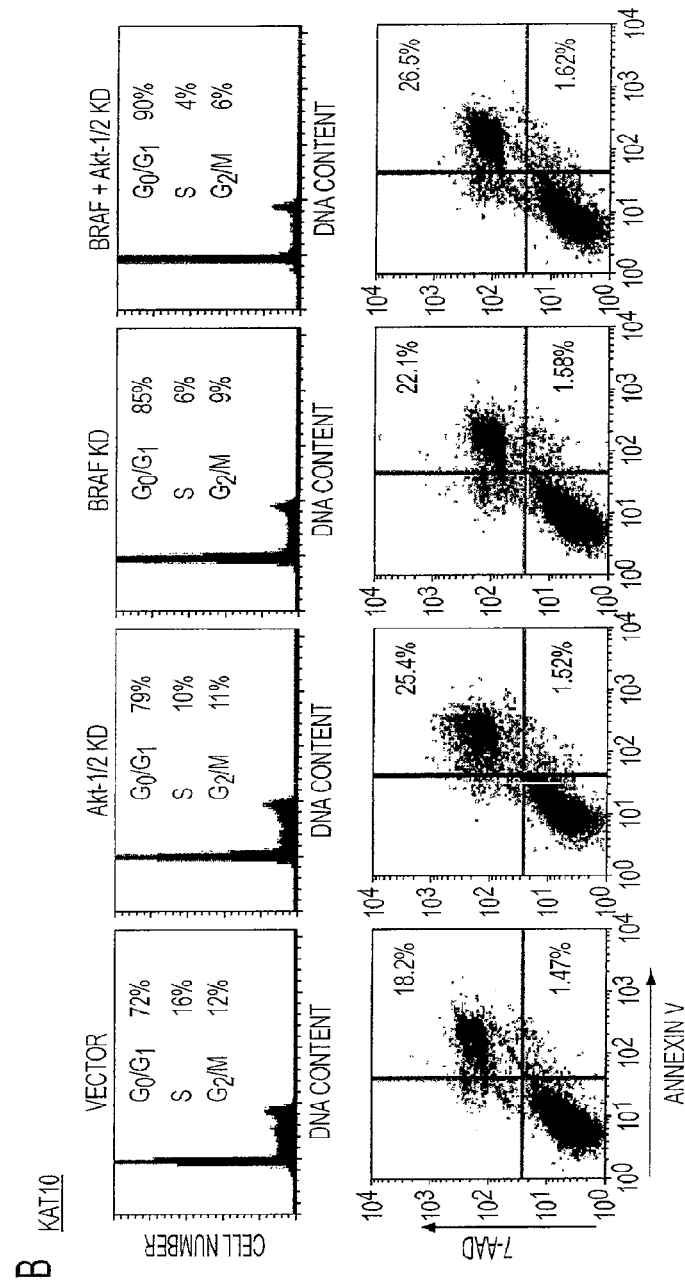

Promotion of $G_0/G_1$ Cell Cycle Arrest and Apoptosis by siRNA Knockdown of Akt-1/2 and BRAF To investigate further the cellular events involved in the inhibition of cell proliferation by dual suppression of PI3K/Akt and MAP kinase pathways, we transiently transfected Akt-1/2 and BRAF siRNA in NPA and KAT10 cells and measured cell cycle and apoptotic patterns by flow cytometric analysis of DNA content and Annexin V staining (FIG. 11). In NPA cells, compared with control vector, siRNA knockdown of Akt-1/2 and BRAF caused an increase in the $G_0/G_1$ fraction from 65.9% to 74.2% (by 12.6%) and to 81.5% (by 23.7%), respectively (FIG. 11A, upper panel). With dual knockdown of Akt-1/2 and BRAF, there was a dramatic synergistic increase in the sub-$G_0$ fraction in comparison with control vector or knockdown of Akt-1/2 or BRAF alone (9.5% vs. 0.4-1.4%), reflecting increased cell apoptosis, and the $G_0/G_1$ fraction was correspondingly only moderately increased. These data were consistent with the apoptotic patterns shown in FIG. 11A, lower panel, which showed a dramatic increase in both early and late apoptosis (9.7% and 13.4%, respectively) with dual knockdown of Akt-1/2 and BRAF. In contrast, knockdown of Akt-1/2 or BRAF alone had a much smaller effect on cell apoptosis. In KAT10 cells, siRNA knockdown of Akt-1/2 and BRAF increased the $G_0/G_1$ fraction from 72% to 79% (by 10%) and 85% (by 18%), respectively, and to 90% (by 25%) with dual knockdown of Akt-1/2 and BRAF (FIG. 11B, upper panel). An increase, albeit modest, in late apoptosis was also seen with individual or dual knockdown of Akt-1/2 and BRAF in KAT-10 cells (FIG. 11B, lower panel). These data suggest that both increased $G_0/G_1$ cell cycle arrest and cell apoptosis were involved in the inhibition of NPA and KAT-10 cell growth by suppression of PI3K/Akt and MAP kinase pathways, which were most pronounced with dual knockdown of the PI3K/Akt and MAP kinase pathways.

Example 11

Figure 12:
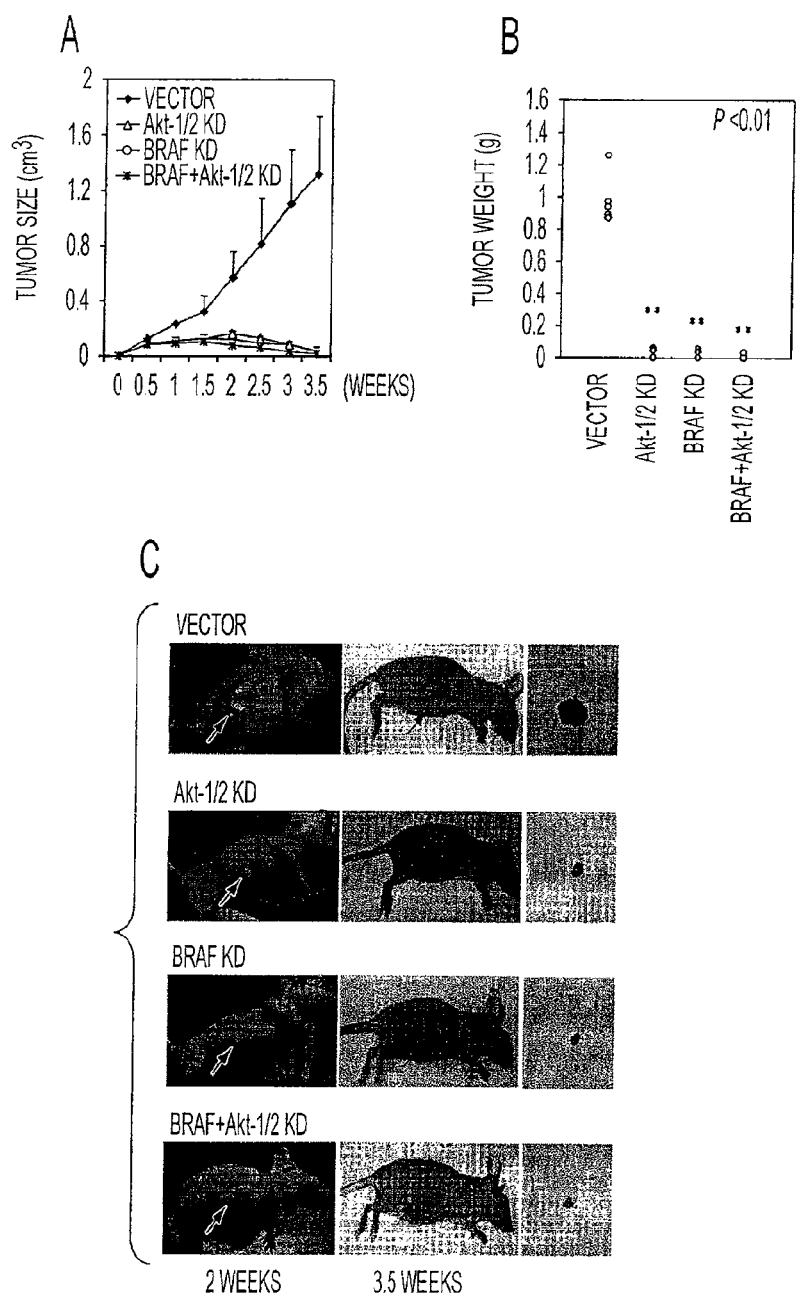
FIG. 12A-12C. Effects of stable siRNA knockdown of Akt-1/2 and BRAF, individually or dually, on in vivo growth of thyroid cancer. KAT10 cells were stably transfected with specific siRNAs to knock down Akt-1/2 and BRAF, individually or dually as described in FIG. 9. Cells were injected subcutaneously into the flank of nude mice (n=5 in each group), and the animals were subsequently monitored for tumor growth.

Inhibition of Tumorigenicity and In Vivo Tumor Growth of Thyroid Cancer Cells by Stable siRNA Knockdown of Akt-1/2 and BRAF To more directly assess the therapeutic potential of targeting PI3K/Akt and MAP kinase pathways for thyroid cancer, we tested the effects of knockdown of these pathways on tumor formation and growth from KAT-10 cells in nude mice. As shown in FIG. 12, emerging tumors became visible in most mice within 0.5 wk after inoculation of cells. Although the tumor volume progressively grew in all groups, a much slower pace was seen with siRNA knockdown of Akt-1/2 and BRAF and dual knockdown of the two (FIG. 12A). After two weeks, tumors started shrinking in all the siRNA knockdown groups while tumors in the control group continued to grow. As knockdown of Akt-1/2 and BRAF each alone already caused a remarkable inhibition of tumor growth, dual knockdown of the two only slightly further decreased the tumor size (FIGS. 12B and 12C). Some tumors in the siRNA knockdown groups virtually disappeared at 3.5 wk. At this time, the average weight of the tumors in the 4 groups (each with n=5) were 0.99±0.16 g for the control, 0.03±0.03 g for Akt-1/2 siRNA knockdown, 0.03±0.03 g for BRAF siRNA knockdown, and 0.014±0.02 g for dual knockdown, respectively (mean±SD; P<0.01). FIG. 12B shows the tumor weight of each individual mouse in all groups, more clearly illustrating the inhibition of the tumor by specific Akt-1/2 and BRAF knockdown individually or in combination. FIG. 12C shows representative tumors from the control and the three siRNA knockdown groups before and after surgical removal.

Example 12

Figure 13:
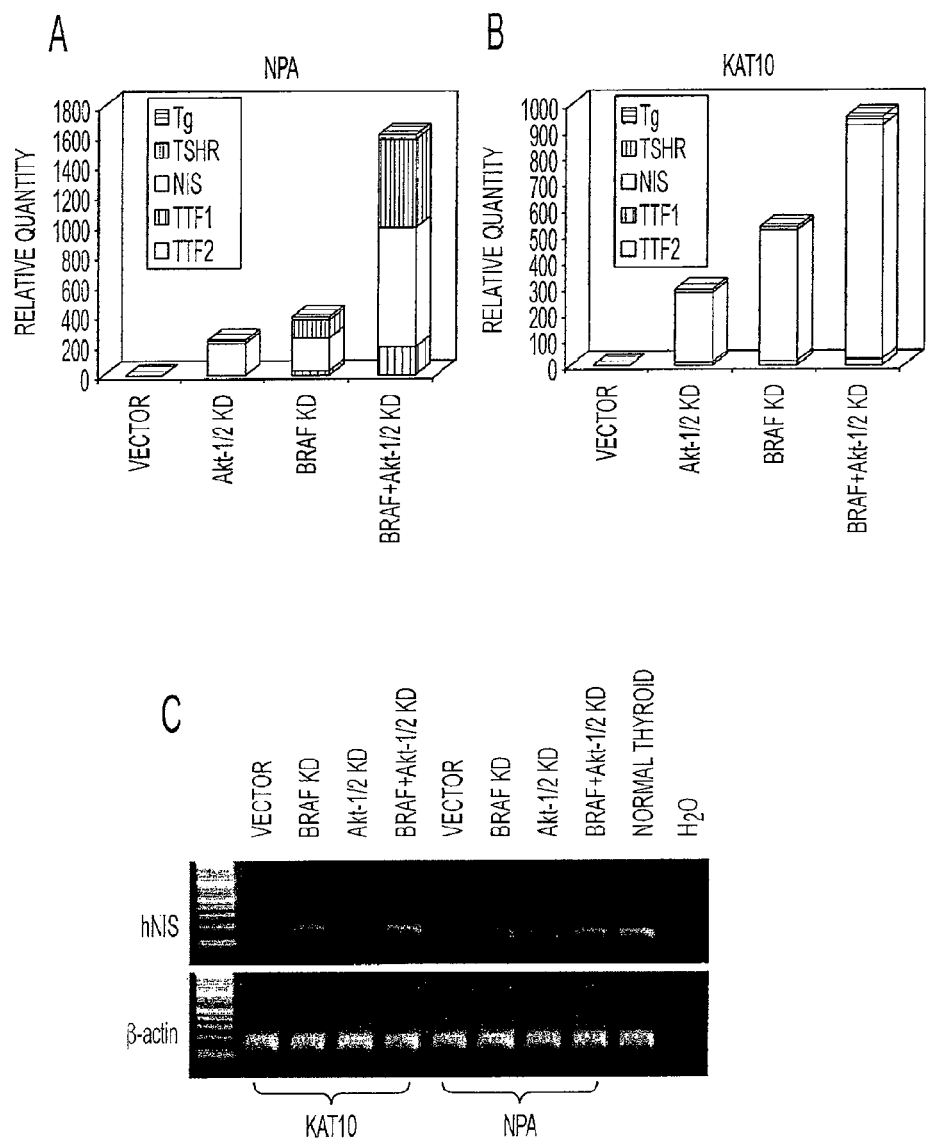
FIG. 13A-13C. Effects of stable siRNA knockdown of Akt-1/2 and BRAF, individually or dually, on the expression of thyroid iodide-metabolizing genes. NPA and KAT10 cells were stably transfected with specific siRNAs to knock down Akt-1/2 and BRAF, individually or dually as described in FIG. 9. After a serum starvation for 24 h, total RNA was isolated for expression analysis for the indicated thyroid iodide-metabolizing genes. Quantitative real-time PCR analysis was performed for the expression of thyroid genes, including Tg, TSHR, NIS, TTF1, and TTF2 in NPA (FIG. 13A) and KAT10 (FIG. 13B) cells.

Restoration of Iodide-Metabolizing Gene Expression by Stable siRNA Knockdown of Akt-1/2 and BRAF We next assessed the restorability of thyroid gene expression by suppression of the PI3K/Akt and MAP kinase pathways in NPA and KAT-10 cells with stable siRNA knockdown of Akt-1/2 and BRAF. As shown in FIG. 13A, expression of NIS, TSHR, and TTF1 could be restored by siRNA knockdown of BRAF and only expression of NIS could be restored by Akt-1/2 knockdown. Remarkably, dual knockdown of Akt-1/2 and BRAF had a dramatic synergistic effect on the expression of these genes (FIG. 13A). In KAT-10 cells, Akt-1/2 and BRAF knockdown individually could only restore the expression of NIS (FIG. 13B). Their dual knockdown synergized the expression of NIS. Expression of Tg and TSHR could be slightly restored by dual siRNA knockdown of Akt-1/2 and BRAF (FIG. 13B). RT-PCR confirmed the expression of NIS (FIG. 13C), which was consistent with the results of quantitative real-time PCR (FIGS. 13A and B).

Example 13

Figure 14:
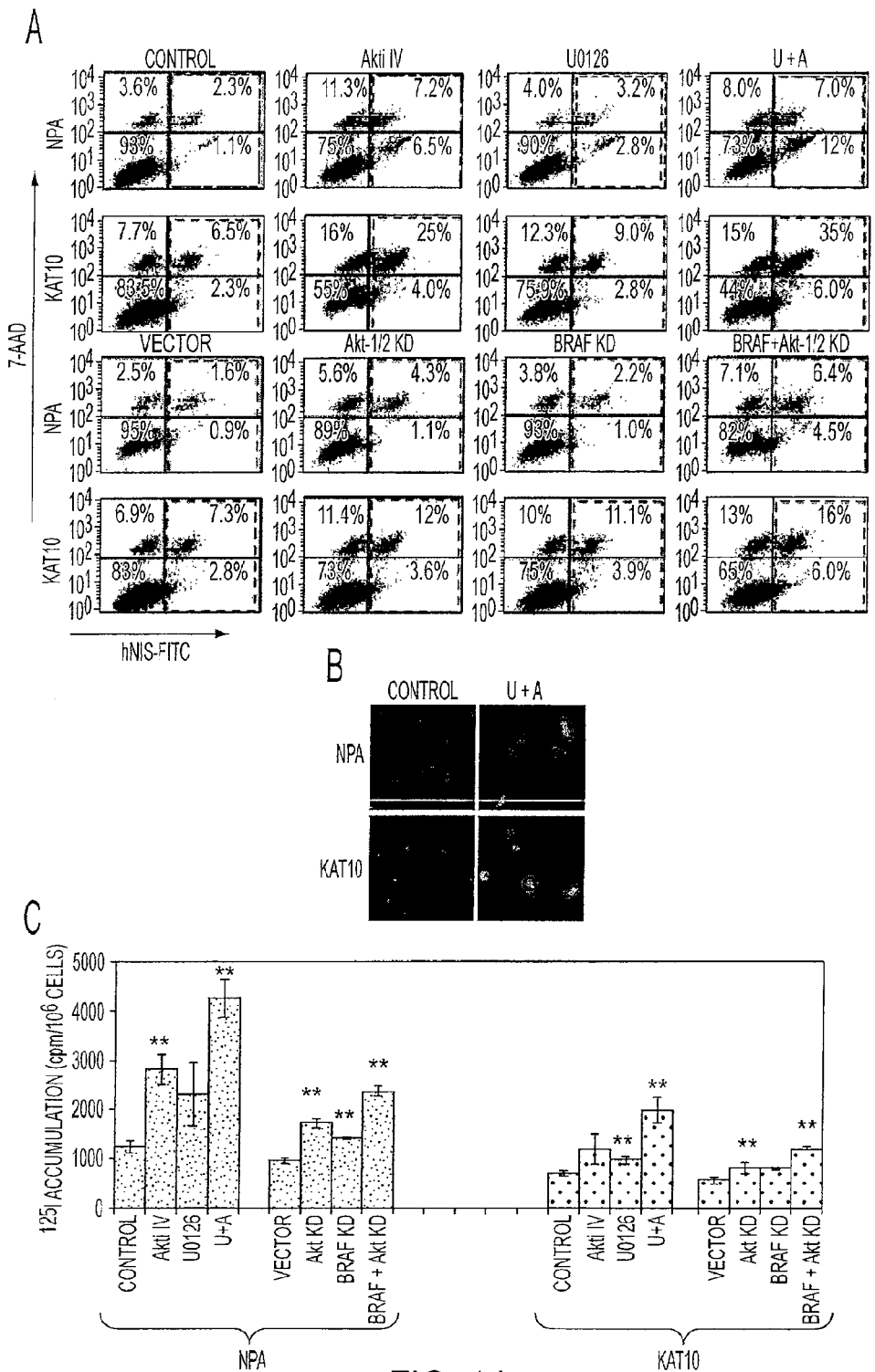
FIG. 14A-14C. Effects of suppression of PI3K/Akt and MAP kinase pathways, individually or in combination, on the expression of NIS protein and radioiodide uptake in thyroid cancer cells.

Restoration of NIS Protein Expression and the Ability to Take Up Radioiodine in Thyroid Cancer Cells by Suppression of PI3K/Akt and MAP Kinase Pathways To specifically investigate the effect of suppression of PI3K/Akt and MAP kinase pathways on the expression of NIS protein, NPA and KAT10 cells were treated with specific inhibitors (Akti IV for Akt, and U0126 for MEK) or stably transfected with various siRNA constructs. In NPA cells, Akti IV and U0126 increased the NIS expression from 3.4% to 13.7% and 6%, respectively, and to 19% with combination of the two (FIG. 14A, upper panel). In KAT10 cells, Akti IV and U0126 increased the NIS expression from 8.8% to 29% and 11.8%, respectively, and to 41% with combination of the two (FIG. 14A, upper panel). Although both Akti IV and U0126 induced NIS protein expression, Akti IV showed a more pronounced effect in both NPA and KAT10 cells (FIG. 14A, upper panel). Consistent with the quantitative real-time PCR results on mRNA expression (FIG. 14C), combination of Akti IV and U0126 showed significantly enhanced or synergized effects on NIS protein expression (FIG. 14A, upper panel). Similarly, siRNA knockdown of Akt-1/2 and BRAF could each increase the NIS protein expression, albeit modestly, and dual knockdown of Akt-1/2 and BRAF showed enhanced effects in both NPA and KAT10 cells (FIG. 14A, lower panel). We also performed immunofluorescent microscopy, which showed that dual inhibition of PI3K/Akt and MAP kinase pathways by Akti IV and U0126 robustly restored the expression of NIS protein on the membranes of NPA and KAT10 cells (FIG. 14B).

Given the restoration of expression of thyroid iodide-metabolizing genes in NPA and KAT10 cells by suppression of PI3K/Akt and MAP kinase pathways, we examined functionally the ability of these cells to take up radioiodide. As shown in FIG. 14C, treatment of NPA and KAT10 cells with U0126 or Akti IV significantly increased Na$^{125}$I uptake and combination of the two inhibitors showed an enhanced effect. Stable knockdown of Akt-1/2 or BRAF could also increase radioiodide uptake, which was enhanced with dual knockdown of the two, albeit less robustly compared with drug treatments. Compared with KAT10 cells, radioiodine uptake was more pronounced in NPA cells (FIG. 14C), consistent with the pattern of NIS protein expression that was also more pronounced in living NPA cells (FIG. 14A).

Example 14

Materials and Methods for Examples 7-13

Cell Culture

Human thyroid cancer NPA and KAT10 cells, which were poorly differentiated or undifferentiated cancer cell lines (Fagin J A, Matsuo K, Karmakar A, Chen D L, Tang S H, Koeffler H P. High prevalence of mutations of the p53 gene in poorly differentiated human thyroid carcinomas. *J Clin Invest*. 1993; 91:179-184; van Staveren W C, Solis D W, Delys L, et al. Human thyroid tumor cell lines derived from different tumor types present a common dedifferentiated phenotype. *Cancer Res*. 2007; 67:8113-8120), were from Dr. Guy J. F. Juillard (University of California-Los Angeles School of Medicine, Los Angeles, Calif.) and Dr. Kenneth B. Ain (University of Kentucky Medical Center, Lexington, Ky.), respectively. Both of the two thyroid cancer cells lines harbor genetic alterations that could activate both PI3K/Akt and MAP kinase pathways: BRAF V600E (homozygous) and PIK3CA amplification for NPA cells and BRAF V600E (heterozygous) and PIK3CA amplification for KAT10 cells. Cell lines were routinely grown at 37° C. in RPMI 1640 medium with 10% fetal bovine serum (FBS) and 5% carbon dioxide. For NPA cells, 77 mg sodium pyruvate (Irvine Scientific, Santa Ana, Calif.), 750 mg sodium bicarbonate (Invitrogen), 7 mL of 100×MEM nonessential amino acid (Irvine Scientific), 5 mL of 100× antimycotic solution (Omega Scientific, Tarzana, Calif.), and 1 mL of 50 mg/mL gentamicin (Invitrogen), in each 500 mL medium, were also supplemented. In some experiments, to block the PI3K/Akt and MAP kinase pathways, the Akt inhibitor IV (Akti IV) (Calbiochem, Darmstadt, Germany) and the MEK inhibitor U0126 (Sigma-Aldrich, St. Louis, Mo., USA) were added to the culture at the indicated time and concentrations, with dimethyl sulphoxide (DMSO) as the vehicle and control.

Later work of third parties revealed that the KAT-10 cells which we used are actually colon cancer cells derived from H29 cells. Schweppe R E, Klopper J P, Korch C, Pugazhenthi U, Benezra M, Knauf J A, Fagin J A, Marlow L A, Copland J A, Smallridge R C, Haugen B R. Deoxyribonucleic acid profiling analysis of 40 human thyroid cancer cell lines reveals cross-contamination resulting in cell line redundancy and misidentification. J Clin Endocrinol Metab. 2008 November; 93(11):4331-41. Epub 2008 Aug. 19.

Lentivirus-Mediated RNA Interference of Akt-1, Akt-2, and BRAF

The lentiviral pSicoR-PGK-GFP and pSicoR-PGK-puro vectors (Addgene Inc. Cambridge, Mass., USA) encoding hairpin RNA sequences were used to knock-down specific Akt-1, Akt-2 and BRAF. The hairpin sequences used for BRAF, Akt-1, Akt-2, and combined Akt-1 and Akt-2 (Akt-1/2) were presented in Table 1. To generate lentiviral particles, human embryonic kidney 293 cells (ATCC, Manassas, Va., USA) were co-transfected with the lentiviral vector and compatible packaging plasmid mixture using Lipofectamine 2000 (Invitrogen), following the manufacturer's instructions. NPA and KAT-10 cells were exposed to lentivirus-containing supernatant for 16 hours in the presence of Polybrene (Sigma). After 3-4 days, the cells were serum-starved (0.5% FBS) and harvested 24 hours later in RIPA lysis buffer. Western blotting assays were performed to detect the protein expression of Akt-1, Akt-2, and BRAF.

Western Blotting Assay

Cells were lysed in RIPA buffer (Santa Cruz, Calif.). Cellular proteins were resolved by electrophoresis on a SDS-polyacrylamide (10%) gel (SDS-PAGE), transferred onto PVDF membranes (Amersham Pharmacia Biotech, Piscataway, N.J.), and immunoblotted with specific primary antibodies. Anti-BRAF (Sc-166), anti-phospho-Akt-1/2/3 (Sc-7985-R), anti-phospho-ERK (Sc-7383), and anti-Actin (Sc-1616-R) were purchased from Santa Cruz (Santa Cruz, Calif.). Anti-Akt-1 (#2967) and anti-Akt-2 (#2964) were purchased from Cell Signaling Technologies, Inc. (Beverly, Mass.). Antigen-antibody complexes were visualized using HRP-conjugated anti-mouse (Sc-2005, Santa Cruz, Calif.) or anti-rabbit (Sc-2004, Santa Cruz, Calif.) IgG antibodies and ECL Western Blotting Analysis System (Amersham Pharmacia).

Cell Proliferation Assay

Cells (800/well) were seeded into a 96-well plate and cultured with 2.5% FBS. MTT assay was performed daily over a 5-day time course to evaluate cell numbers using a MTT cell proliferation assay kit (ATCC, Manassas, Va., USA) following the manufacturer's instructions.

Colony Formation Assay

For soft-agar colony-formation assay, $1\times10^5$ cells were plated into 6-well plates with a bottom layer of 0.6% agar and a top layer of 0.3% agar. Following hardening of soft agar, plates were incubated at 37° C. with 5% $CO_2$. After 2-3 weeks of culture, colonies were counted and photographed under a microscope.

Cell Invasion Assay

Cell invasion was assayed in triplicates using Matrigel-coated Transwell cell culture chambers (#354481, BD Biosciences) according to the instructions of the manufacturer. Briefly, cells ($1.5\times10^5$ cells/well) suspended in serum-free medium were placed in the upper chamber of the Transwell insert, and RPMI 1640 medium containing 10% FBS was added to the lower chamber. Following a 24 h-incubation at 37° C. with 5% $CO_2$, non-invasive cells in the upper chamber were removed and invasive cells were fixed in 100% methanol and stained with 0.5% crystal violet in 2% ethanol. The numbers of invasive cells were photographed and counted under a microscope.

Cell Cycle Analysis

Cells were harvested, washed twice in PBS, and resuspended in 70% ethanol on ice for at least 30 min. After centrifugation, $1\times10^6$ thyroid cancer cells transiently transected with various siRNA constructs were resuspended in 1 ml of propidium iodide staining solution (50 µg of propidium iodide, 1 mg of RNase A, and 1 mg of glucose per 1 ml PBS) and incubated at room temperature for 30 min. Cell cycles were analyzed based on DNA contents by FACS using a LSR Flow Cytometer (BD Biosciences, NJ).

Apoptosis Assay

Thyroid cancer cells were transiently transfected with various siRNA constructs. Cells were serum-starved for 24 h, followed by culture in medium containing 10% FBS for 24 h as described (Yamane K, Tateishi K, Klose R J, et al. PLU-1 is an H3K4 demethylase involved in transcriptional repression and breast cancer cell proliferation. *Mol Cell.* 2007; 25:801-812). Cells were harvested, washed with PBS, and subjected to sequential staining with Annexin V-PE Apoptosis Detection Kit (BD Biosciences) by two-color flow cytometry, according to the manufacturer's protocol. Cells that were Annexin V-positive and 7-AAD-negative served as early apoptotic population. Cells that were both Annexin V- and 7-AAD-positive served as late apoptotic population.

Xenograft Tumor Assay in Nude Mice

Puromycin-selected and stably transfected cells were grown to approximately 80-90% confluence and harvested with 0.25% Trypsin/1 mM EDTA solution. Five$\times10^6$ cells in 100 µl of RPMI 1640 medium were injected into the flanks of nude mice (five for each group) at the age of about 5-week (Harlan Sprague Dawley, Indianapolis, Ind.). Tumor growth was evaluated by measuring the size of the tumor on the skin surface and photographed twice a week. The tumor volume is calculated by the formula "volume=(width)$^2\times$length/2," as previously described (Gray M J, Wey J S, Belcheva A, et al. Neuropilin-1 suppresses tumorigenic properties in a human pancreatic adenocarcinoma cell line lacking neuropilin-1 coreceptors. *Cancer Res.* 2005; 65:3664-3670). At the end of experiment, mice were scarified, and the developed tumors were surgically removed, weighted, and photographed.

RNA Extraction and Quantitative RT-PCR Analysis

Total RNA was isolated using TRIzol™ reagent according to the instructions of the manufacturer (Invitrogen). Normal human thyroid RNA samples purchased from Stratagene (La Jolla, Calif.) were used as positive control. The reverse transcription synthesis of cDNA was conducted with the SuperScript First-Strand Synthesis kit (Invitrogen), following the manufacturer's instruction. Quantitative real-time PCR analysis was performed to evaluate expression of thyroid genes on an ABI Prism 7900HT Sequence Detector (Applied Biosystems), using SYBR Green PCR Core Reagents kit according to the instructions of the manufacturer (Applied Biosystems). The expression value of each gene was normalized to the amount of β-actin cDNA to calculate the relative amount of RNA present in each sample. The primers of intron-spanning thyroid-specific genes, Tg, TSHR, NIS, TTF1 and TTF2, were designed using Primer Express (Applied Biosystems, CA) and presented in Table 2. A semi-quantitative RT-PCR amplification was also carried out to amplify hNIS, using the primers 5'-TCC ATG TAT GGC GTG AAC C-3' (forward; SEQ ID NO: 1) and 5'-CTT CGA AGA TGT CCA GCA CC-3' (reverse; SEQ ID NO: 2). The JI-actin gene was run in parallel for quality control, using the primers 5'-TCT ACA ATG AGC TGC GTG TG-3' (forward; SEQ ID NO: 3) and 5'-TAG ATG GGC ACA GTG TGG GT-3' (reverse; SEQ ID NO: 4). PCR products were resolved by 1.5% agarose gel electrophoresis and visualized by ethidium bromide staining.

Flow Cytometry Analysis of hNIS Expression

Thyroid cancer cells treated with specific inhibitors and various siRNA constructs to induce the expression of NIS were incubated with VJ2 α-NIS mAb (a gift from Dr. Sabine Costagliola at the Free University of Brussels) (Pohlenz J, Duprez L, Weiss R E, Vassart G, Refetoff S, Costagliola S. Failure of membrane targeting causes the functional defect of two mutant sodium iodide symporters. *J Clin Endocrinol Metab.* 2000; 85:2366-2369) diluted at 1:20 in FACS buffer (3% FBS, 0.02% NaN$_3$ in PBS) at 4° C. for 1 h. Cells were then washed once with FACS buffer and incubated with FITC-conjugated α-mouse IgG (Sigma) diluted at 1:100 in FACS buffer at 4° C. for 1 h. Cells were washed again in FACS buffer, resuspended in 2 ml of FACS buffer with 7-AAD, and analyzed by FACS using a LSR Flow Cytometer (BD Biosciences, NJ). Secondary antibody alone was used as a negative control. Fluorescent microscopic examination was conducted to monitor NIS expression (Nikon Corporation, Tokyo, Japan).

Radioactive Iodide Uptake (RAIU) Assay

Thyroid cancer cells ($1\times10^6$ cells/well) treated under the indicated conditions were seeded in 12-well plates. Cells in 0.5 ml/well were incubated with RPMI 1640 medium containing 1 µCi Na$^{125}$I and 5 µM non-radioactive NaI for 1 h at 37° C. with 5% $CO_2$. Subsequently, the medium was aspirated and cells were quickly washed twice with ice-cold Hank's balanced salt solution (HBSS) and harvested with tripsin-EDTA. Cells were collected and radioactivity was counted by a gamma-counter.

Statistical Analysis

Except for the animal studies, all the experiments were similarly done at least three times. Statistical analysis for pair comparison was performed using t-test.

REFERENCES

The disclosure of each reference cited is expressly incorporated herein.

1. Jemal A, Devesa S S, Hartge P, Tucker M A. Recent trends in cutaneous melanoma incidence among whites in the United States. J Natl Cancer Inst 2001; 93:678-83.
2. Lasithiotakis K G, Leiter U, Gorkievicz R, et al. The incidence and mortality of cutaneous melanoma in Southern Germany: trends by anatomic site and pathologic characteristics, 1976 to 2003. Cancer 2006; 107:1331-9.
3. Ries L A G, Melbert D, Krapcho M, et al. (eds). SEER Cancer Statistics Review, 1975-2005, National Cancer Institute. Bethesda, Md., http://seer.cancer.gov/csr/1975_2005/, based on November 2007 SEER data submission, posted to the SEER web site, 2008.
4. Flaherty K T. Chemotherapy and targeted therapy combinations in advanced melanoma. Clin Cancer Res 2006; 12:2366s-70s.
5. Tawbi H A, Kirkwood J M. Management of metastatic melanoma. Semin Oncol 2007; 34:532-45.
6. Davies H, Bignell G R, Cox C, et al. Mutations of the BRAF gene in human cancer. Nature 2002; 417:949-54.
7. Wu H, Goel V, Haluska F G. PTEN signaling pathways in melanoma. Oncogene 2003 22:3113-22.
8. Curtin J A, Fridlyand J, Kageshita T, et al. Distinct sets of genetic alterations in melanoma. N Engl J Med 2005; 353:2135-47.
9. Marquette A, Bagot M, Bensussan A, Dumaz N. Recent discoveries in the genetics of melanoma and their therapeutic implications. Arch Immunol Ther Exp (Warsz) 2007; 55:363-72.
10. Satyamoorthy K, Li G, Gerrero M R, et al. Constitutive mitogen-activated protein kinase activation in melanoma is mediated by both BRAF mutations and autocrine growth factor stimulation. Cancer Res 2003; 63:756-9.
11. Stahl J M, Sharma A, Cheung M, et al. Deregulated Akt3 activity promotes development of malignant melanoma. Cancer Res 2004; 64:7002-10.
12. Dai D L, Martinka M, Li G. Prognostic significance of activated Akt expression in melanoma: a clinicopathologic study of 292 cases. J Clin Oncol 2005; 23:1473-82.
13. Meier F, Schittek B, Busch S, et al. The RAS/RAF/MEK/ERK and PI3K/AKT signaling pathways present molecular targets for the effective treatment of advanced melanoma. Front Biosci 2005; 10:2986-3001.
14. Meier F, Busch S, Lasithiotakis K, et al. Combined targeting of MAPK and AKT signalling pathways is a promising strategy for melanoma treatment. Br J Dermatol 2007; 156:1204-13.
15. Kwong L, Chin L, Wagner S N. Growth factors and oncogenes as targets in melanoma: lost in translation? Adv Dermatol 2007; 23:99-129.
16. Faivre J, Clerc J, Gérolami R, et al. Long-term radioiodine retention and regression of liver cancer after sodium iodide symporter gene transfer in Wistar rats. Cancer Res 2004; 64:8045-51.
17. Dwyer R M, Bergert E R, O'connor M K, et al. In vivo radioiodide imaging and treatment of breast cancer xenografts after MUC1-driven expression of the sodium iodide symporter. Clin Cancer Res 2005; 11:1483-9.
18. Riesco-Eizaguirre G, Santisteban P. A perspective view of sodium iodide symporter research and its clinical implications. Eur J Endocrinol 2006; 155:495-512.
19. Schipper M L, Riese C G, Seitz S, et al. Efficacy of 99mTc pertechnetate and 131I radioisotope therapy in sodium/iodide symporter (NIS)-expressing neuroendocrine tumors in vivo. Eur J Nucl Med Mol Imaging 2007; 34:638-50.
20. Willhauck M J, Sharif Samani B R, Klutz K, et al. Alpha-fetoprotein promoter-targeted sodium iodide symporter gene therapy of hepatocellular carcinoma. Gene Ther 2008; 15:214-23.
21. Nilsson M. Iodide handling by the thyroid epithelial cell. Exp Clin Endocrinol Diabetes 2001; 109:13-17.
22. Mian C, Lacroix L, Bidart J.-M, Caillou B, Filetti S, Schlumberger M. Sodium/iodide symporter in thyroid cancer. Exp Clin Endocrinol Diabetes 2001; 109: 47-51.
23. Duntas L H, Cooper D S. Review on the occasion of a decade of recombinant human TSH: prospects and novel uses. Thyroid 2008; 18(5):509-16.
24. Xing M, Westra W H, Tufano R P, et al. BRAF mutation predicts a poorer clinical prognosis for papillary thyroid cancer. J Clin Endocrinol Metab 2005; 90:6373-9.
25. Riesco-Eizaguirre G, Gutierrez-Martinez P, Garcia-Cabezas M A, Nistal M, Santisteban P. The oncogene BRAF V600E is associated with a high risk of recurrence and less differentiated papillary thyroid carcinoma due to the impairment of Na+/I− targeting to the membrane. Endocr Relat Cancer 2006; 13:257-69.
26. Mian C, Barollo S, Pennelli G, et al. Molecular characteristics in papillary thyroid cancers (PTCs) with no (131)I uptake. Clin Endocrinol 2008; 68:108-16.
27. Durante C, Puxeddu E, Ferretti E, et al. BRAF mutations in papillary thyroid carcinomas inhibit genes involved in iodine metabolism. J Clin Endocrinol Metab 2007; 92:2840-3.
28. Giordano T J, Kuick R, Thomas D G, et al. Molecular classification of papillary thyroid carcinoma: distinct BRAF, RAS, and RET/PTC mutation-specific gene expression profiles discovered by DNA microarray analysis. Oncogene 2005; 24:6646-56.
29. Di Cristofaro J, Silvy M, Lanteaume A, Marcy M, Carayon P, De Micco C. Expression of tpo mRNA in thyroid tumors: quantitative PCR analysis and correlation with alterations of ret, Braf, ras and pax8 genes. Endocr Relat Cancer 2006; 13:485-95.
30. Cass L A, Meinkoth J L. Ras signaling through PI3K confers hormone-independent proliferation that is compatible with differentiation. Oncogene. 2000; 19:924-32.
31. Garcia B, Santisteban P. PI3K is involved in the IGF-I inhibition of TSH-induced sodium/iodide symporter gene expression. Mol Endocrinol 2002; 16:342-52.
32. Friday B B and Adjei A A. Advances in targeting the Ras/Raf/MEK/Erk mitogen-activated protein kinase cascade with MEK inhibitors for cancer therapy. Clin Cancer Res 2008; 14:342-6.
33. Ellerhorst J A, Sendi-Naderi A, Johnson M K, Cooke C P, Dang S M, Diwan A H. Human melanoma cells express functional receptors for thyroid-stimulating hormone. Endocr Relat Cancer 2006; 13:1269-77.
34. Fagin J A, Matsuo K, Karmakar A, Chen D L, Tang S H, Koeffler H P. High prevalence of mutations of the p53 gene in poorly differentiated human thyroid carcinomas. J Clin Invest 1993; 91:179-84.
35. Schweppe R E, Klopper J P, Korch C, Pugazhenthi U, Benezra M, Knauf J A, et al. DNA profiling analysis of 40 human thyroid cancer cell lines reveals cross-contamination resulting in cell line redundancy and minidentification. J Clin Endocrinol Metab 2008 Aug. 19. [Epub ahead of print]
36. He S J, Stevens G, Braithwaite A W, Eccles M R. Transfection of melanoma cells with antisense PAX3 oligonucleotides additively complements cisplatin-induced cytotoxicity. Mol Cancer Ther 2005; 4:996-1003.

37. Pohlenz J, Duprez L, Weiss R E, Vassart G, Refetoff S, Costagliola S. Failure of membrane targeting causes the functional defect of two mutant sodium iodide symporters. J Clin Endocrinol Metab 2000; 85:2366-9.
38. Kau T R, Schroeder F, Ramaswamy S, et al. A chemical genetic screen identifies inhibitors of regulated nuclear export of a Forkhead transcription factor in PTEN-deficient tumor cells. Cancer Cell 2003; 4:463-76.
39. Liu D, Liu Z, Condouris S, Xing M. BRAF V600E maintains proliferation, transformation, and tumorigenicity of BRAF-mutant papillary thyroid cancer cells. J Clin Endocrinol Metab 2007; 92:2264-71.
40. Ball D W, Jin N, Rosen D M, et al. Selective growth inhibition in BRAF mutant thyroid cancer by the mitogen-activated protein kinase kinase 1/2 inhibitor AZD6244. J Clin Endocrinol Metab 2007; 92:4712-8.
41. Boisvert-Adamo K, Aplin A E. B-RAF and PI-3 kinase signaling protect melanoma cells from anoikis. Oncogene 2006; 25:4848-56.
42. Mazzaferri E L: An overview of the management of thyroid cancer. In: Mazzaferri E L, Harmer C, Mallick U K, Kendall-Taylor P, eds. Practical Management of Thyroid Cancer: A Multidisciplinary Approach. London, England: Springer-Verlag 1-28, 2006.
43. Cooper D S, Doherty G M, Haugen B R, et al. The American Thyroid Association Guidelines Taskforce. Management guidelines for patients with thyroid nodules and differentiated thyroid cancer. Thyroid 2006; 16:109-42.
44. Xing M. BRAF mutation in papillary thyroid cancer: pathogenic role, molecular bases, and clinical implications. Endocr Rev 2007; 28:742-62.
45. Baker C H, Morris J C. The sodium-iodide symporter. Curr Drug Targets Immune Endocr Metabol Disord 2004; 4:167-74.
46. Buchsbaum D J, Chaudhuri T R, Zinn K R. Radiotargeted gene therapy. J Nucl Med 2005; 46 Suppl 1:179S-86S.

The invention claimed is:

1. A method of treating a human cancer in a patient comprising: administering an inhibitor of a PI3K/Akt pathway protein or its expression to the patient; and administering an inhibitor of a MAP kinase pathway protein or its expression to the patient, wherein the inhibitors are administered in sufficient amounts to induce expression of one or more iodide-handling genes in the human cancer.

2. The method of claim 1 further comprising: administering radioiodine to the patient.

3. A method of treating a human cancer in a patient comprising: administering an inhibitor of a PI3K/Akt pathway protein or its expression or an inhibitor of a MAP kinase pathway protein or its expression to the patient in sufficient amounts to induce expression of one or more iodide-handling genes in the human cancer; and administering radioiodine to the patient.

4. The method of claim 3 wherein the radioiodine is administered subsequent to the administering of the inhibitors.

5. The method of claim 3 wherein the human cancer is a thyroid tumor.

6. The method of claim 3 wherein the human cancer is a melanoma.

7. The method of claim 3 wherein the human cancer is a non-thyroid tumor.

8. The method of claim 3, wherein the cancer has an activating mutation in the PI3K/Akt pathway.

9. The method of claim 8 wherein the mutation is selected from the group consisting of PIK3CA mutation, PIK3D mutation, PIK3B mutation, Ras mutation, PTEN mutation, and PI3KCA amplification.

10. The method of claim 8 wherein the mutation is in a receptor tyrosine kinase gene.

11. The method of claim 1 wherein the cancer has an activating mutation in the MAP kinase pathway.

12. The method of claim 11 wherein the cancer has an activating mutation selected from the group consisting of: BRAF mutation, RET/PTC rearrangement, Ras mutation, MEK mutation, and ERK mutation.

13. The method of claim 3, wherein the cancer has an activating mutation in PI3K.

14. The method of claim 1 wherein the cancer has an activating mutation in MAP kinase.

15. The method of claim 1 wherein the cancer has activating mutations in both PI3K/Akt and MAP kinase pathways.

16. The method of claim 3 wherein the cancer is a poorly differentiated or undifferentiated thyroid tumor.

17. The method of claim 3 wherein prior to administration of the inhibitors, the cancer is non-responsive to radioiodine treatment.

18. The method of claim 3 wherein a thyroid stimulating hormone is administered to the patient in an amount sufficient to induce expression of one or more iodide-handling genes in the cancer.

19. The method of claim 3, wherein a PI3K/Akt pathway protein inhibitor is administered which is selected from the group consisting of perifosine, triciribine, temsirolimus, everolimus, motesanib, axitinib, sunitinib, Wortmanin, LYS 294002, and AktiIV.

20. The method of claim 1 wherein a MAP kinase pathway protein inhibitor is administered which is selected from the group consisting of CI-1040, PD325901, PD184352, AZD6344, ARRY-142886, RDEA119, RDEA436, RDEA119, PLX4720, BAY43-9006 (sorafenib) and U0126.

21. The method of claim 3, wherein a PI3K/Akt pathway expression inhibitor is administered which is siRNA.

22. The method of claim 1 wherein a MAP kinase pathway expression inhibitor is administered which is siRNA.

23. The method of claim 3, wherein the cancer is selected from the group consisting of salivary, lacrimal, stomach, colon, liver, and breast cancer.

24. The method of claim 1 wherein a MAP kinase pathway expression inhibitor is administered which is selected from the group of siRNA consisting of Ras, RAF, MEK1, MEK2, ERK1, and ERK2 siRNA.

25. The method of claim 3 wherein the one or more iodide-handling genes are selected from the group consisting of the sodium/iodide symporter, thyroid stimulating hormone receptor, thyroglobulin, thyroperoxidase, pendrin, and thyroid transcription factors TTF-1, TTF-2, and PAX8.

26. A method of treating a melanoma or thyroid cancer in a human comprising: administering an inhibitor of a PI3K/Akt pathway protein or its expression and an inhibitor of a MAP kinase pathway protein or its expression to the patient in sufficient amounts to induce expression of one or more iodide-handling genes in the melanoma or thyroid cancer; and administering radioiodine to the human.

* * * * *

SEQUENCE LISTING

```
<160> NUMBER OF SEQ ID NOS: 40

<210> SEQ ID NO 1
<211> LENGTH: 19
<212> TYPE: DNA
<213> ORGANISM: Homo sapiens

<400> SEQUENCE: 1
tccatgtatg gcgtgaacc                                                    19

<210> SEQ ID NO 2
<211> LENGTH: 20
<212> TYPE: DNA
<213> ORGANISM: Homo sapiens

<400> SEQUENCE: 2
cttcgaagat gtccagcacc                                                   20

<210> SEQ ID NO 3
<211> LENGTH: 20
<212> TYPE: DNA
<213> ORGANISM: Homo sapiens

<400> SEQUENCE: 3
tctacaatga gctgcgtgtg                                                   20

<210> SEQ ID NO 4
<211> LENGTH: 20
<212> TYPE: DNA
<213> ORGANISM: Homo sapiens

<400> SEQUENCE: 4
tagatgggca cagtgtgggt                                                   20

<210> SEQ ID NO 5
<211> LENGTH: 55
<212> TYPE: DNA
<213> ORGANISM: Homo sapiens

<400> SEQUENCE: 5
tgcatcaatg gataccgtta ttcaagagat aacggtatcc attgatgctt ttttc            55

<210> SEQ ID NO 6
<211> LENGTH: 55
```

```
<212> TYPE: DNA
<213> ORGANISM: Homo sapiens

<400> SEQUENCE: 6
tgtggtcatg tacgagatga ttcaagagat catctcgtac atgaccactt ttttc      55

<210> SEQ ID NO 7
<211> LENGTH: 59
<212> TYPE: DNA
<213> ORGANISM: Homo sapiens

<400> SEQUENCE: 7
tcgagaaaaa agcatcaatg gataccgtta tctcttgaat aacggtatcc attgatgca   59

<210> SEQ ID NO 8
<211> LENGTH: 59
<212> TYPE: DNA
<213> ORGANISM: Homo sapiens

<400> SEQUENCE: 8
tcgagaaaaa agtggtcatg tacgagatga tctcttgaat catctcgtac atgaccaca   59

<210> SEQ ID NO 9
<211> LENGTH: 20
<212> TYPE: DNA
<213> ORGANISM: Homo sapiens

<400> SEQUENCE: 9
ctatggcctc aagttcctct                                              20

<210> SEQ ID NO 10
<211> LENGTH: 20
<212> TYPE: DNA
<213> ORGANISM: Homo sapiens

<400> SEQUENCE: 10
atcaggagga ggacttcaga                                              20

<210> SEQ ID NO 11
<211> LENGTH: 20
<212> TYPE: DNA
<213> ORGANISM: Homo sapiens

<400> SEQUENCE: 11
gcaaaggctg tgaagcaatt                                              20

<210> SEQ ID NO 12
<211> LENGTH: 20
<212> TYPE: DNA
<213> ORGANISM: Homo sapiens

<400> SEQUENCE: 12
cattgggaag cagatgaagg                                              20

<210> SEQ ID NO 13
<211> LENGTH: 20
<212> TYPE: DNA
<213> ORGANISM: Homo sapiens

<400> SEQUENCE: 13
caggcatggt ggcaggaagt                                              20

<210> SEQ ID NO 14
```

```
<211> LENGTH: 20
<212> TYPE: DNA
<213> ORGANISM: Homo sapiens

<400> SEQUENCE: 14
gctggttttc cctgtctctg                                              20

<210> SEQ ID NO 15
<211> LENGTH: 20
<212> TYPE: DNA
<213> ORGANISM: Homo sapiens

<400> SEQUENCE: 15
tactgcaacg gcaacctggg                                              20

<210> SEQ ID NO 16
<211> LENGTH: 20
<212> TYPE: DNA
<213> ORGANISM: Homo sapiens

<400> SEQUENCE: 16
tctacaatga gctgcgtgtg                                              20

<210> SEQ ID NO 17
<211> LENGTH: 20
<212> TYPE: DNA
<213> ORGANISM: Homo sapiens

<400> SEQUENCE: 17
tcgtggctac aatgtactgc                                              20

<210> SEQ ID NO 18
<211> LENGTH: 20
<212> TYPE: DNA
<213> ORGANISM: Homo sapiens

<400> SEQUENCE: 18
tttgagggca tcagggtcta                                              20

<210> SEQ ID NO 19
<211> LENGTH: 20
<212> TYPE: DNA
<213> ORGANISM: Homo sapiens

<400> SEQUENCE: 19
tgataaagta gtcccgggtg                                              20

<210> SEQ ID NO 20
<211> LENGTH: 20
<212> TYPE: DNA
<213> ORGANISM: Homo sapiens

<400> SEQUENCE: 20
tgttgtcaca gatgacccga                                              20

<210> SEQ ID NO 21
<211> LENGTH: 20
<212> TYPE: DNA
<213> ORGANISM: Homo sapiens

<400> SEQUENCE: 21
acagatggtc aaaggccgtg                                              20
```

```
<210> SEQ ID NO 22
<211> LENGTH: 20
<212> TYPE: DNA
<213> ORGANISM: Homo sapiens

<400> SEQUENCE: 22 agatgggga gactgaaggt                                              20

<210> SEQ ID NO 23
<211> LENGTH: 20
<212> TYPE: DNA
<213> ORGANISM: Homo sapiens

<400> SEQUENCE: 23
ggccatgttc ttgctcacgt                                             20

<210> SEQ ID NO 24
<211> LENGTH: 20
<212> TYPE: DNA
<213> ORGANISM: Homo sapiens

<400> SEQUENCE: 24
tagatgggca cagtgtgggt                                             20

<210> SEQ ID NO 25
<211> LENGTH: 19
<212> TYPE: DNA
<213> ORGANISM: Homo sapiens

<400> SEQUENCE: 25
cctgctaacg actccagca                                              19

<210> SEQ ID NO 26
<211> LENGTH: 20
<212> TYPE: DNA
<213> ORGANISM: Homo sapiens

<400> SEQUENCE: 26
gatattcaac gcatccccag                                             20

<210> SEQ ID NO 27
<211> LENGTH: 20
<212> TYPE: DNA
<213> ORGANISM: Homo sapiens

<400> SEQUENCE: 27
caccaactcc caactttcc                                              20

<210> SEQ ID NO 28
<211> LENGTH: 20
<212> TYPE: DNA
<213> ORGANISM: Homo sapiens

<400> SEQUENCE: 28
acttggatct ccatgtcgct                                             20

<210> SEQ ID NO 29
<211> LENGTH: 20
<212> TYPE: DNA
<213> ORGANISM: Homo sapiens

<400> SEQUENCE: 29
tgcctcacaa ctccatcaga                                             20
```

```
<210> SEQ ID NO 30
<211> LENGTH: 20
<212> TYPE: DNA
<213> ORGANISM: Homo sapiens

<400> SEQUENCE: 30
gctggttttc cctgtctctg                                               20

<210> SEQ ID NO 31
<211> LENGTH: 20
<212> TYPE: DNA
<213> ORGANISM: Homo sapiens

<400> SEQUENCE: 31
accaggacac catgaggaac                                               20

<210> SEQ ID NO 32
<211> LENGTH: 17
<212> TYPE: DNA
<213> ORGANISM: Homo sapiens

<400> SEQUENCE: 32
gcacagagcc tcgcctt                                                  17

<210> SEQ ID NO 33
<211> LENGTH: 20
<212> TYPE: DNA
<213> ORGANISM: Homo sapiens

<400> SEQUENCE: 33
ccagggcacc gtaatagaga                                               20

<210> SEQ ID NO 34
<211> LENGTH: 20
<212> TYPE: DNA
<213> ORGANISM: Homo sapiens

<400> SEQUENCE: 34
agctgctgca gagtcacatc                                               20

<210> SEQ ID NO 35
<211> LENGTH: 19
<212> TYPE: DNA
<213> ORGANISM: Homo sapiens

<400> SEQUENCE: 35
caactgacct cctttgcca                                                19

<210> SEQ ID NO 36
<211> LENGTH: 20
<212> TYPE: DNA
<213> ORGANISM: Homo sapiens

<400> SEQUENCE: 36
gcagtgtgga tttagtgcca                                               20

<210> SEQ ID NO 37
<211> LENGTH: 18
<212> TYPE: DNA
<213> ORGANISM: Homo sapiens

<400> SEQUENCE: 37
caggtctacg atgcgctg                                                 18
```

```
<210> SEQ ID NO 38
<211> LENGTH: 20
<212> TYPE: DNA
<213> ORGANISM: Homo sapiens

<400> SEQUENCE: 38
agatggggga gactgaaggt                                              20

<210> SEQ ID NO 39
<211> LENGTH: 18
<212> TYPE: DNA
<213> ORGANISM: Homo sapiens

<400> SEQUENCE: 39
gctcatgttc atgccgct                                                18

<210> SEQ ID NO 40
<211> LENGTH: 17
<212> TYPE: DNA
<213> ORGANISM: Homo sapiens

<400> SEQUENCE: 40
gttgtcgacg acgagcg                                                 17
```